(12) United States Patent
Jungnickel et al.

(10) Patent No.: US 9,718,594 B2
(45) Date of Patent: Aug. 1, 2017

(54) ORAL CARE INSTRUMENT AND PACKAGE THEREFORE

(71) Applicant: The Procter & Gamble Company, Cincinnati, OH (US)

(72) Inventors: Uwe Jungnickel, Taunus (DE); Niclas Altmann, Schoeneck (DE); Hansjoerg Reick, Steinbach (DE); John Joseph Mertz, Cincinnati, OH (US); Bertholt Schroeder, Cincinnati, OH (US)

(73) Assignee: THE GILLETTE COMPANY LLC, Cincinnati, OH (US)

( * ) Notice: Subject to any disclaimer, the term of this patent is extended or adjusted under 35 U.S.C. 154(b) by 0 days.

(21) Appl. No.: 13/760,236

(22) Filed: Feb. 6, 2013

(65) Prior Publication Data
US 2013/0205528 A1    Aug. 15, 2013

Related U.S. Application Data

(60) Provisional application No. 61/597,350, filed on Feb. 10, 2012.

(51) Int. Cl.
*B65D 83/00* (2006.01)
*B65D 83/10* (2006.01)
(Continued)

(52) U.S. Cl.
CPC .......... *B65D 81/00* (2013.01); *A46B 15/0012* (2013.01); *B65D 75/322* (2013.01);
(Continued)

(58) Field of Classification Search
USPC ......... 206/806, 362.2, 362.3, 471, 470, 774, 206/775, 461, 573, 349, 779, 780, 776,
(Continued)

(56) References Cited

U.S. PATENT DOCUMENTS 757,885 A * 4/1904 Cochrane ............... B44D 3/125
206/209
2,304,227 A * 12/1942 Zafarana .................... 206/362.2
(Continued)

FOREIGN PATENT DOCUMENTS

EP    1 702 584 A1    9/2006

OTHER PUBLICATIONS

PCT International Search Report and Written Opinion dated Jun. 10, 2013.

*Primary Examiner* — J. Gregory Pickett
*Assistant Examiner* — Gideon Weinerth

(57) ABSTRACT

A toothbrush having a handle and a head in a display package is described. The head is attached to a neck which is attached to the handle. An indication element is between the head and the handle and is in electrical communication with a power source. A switch connects the indication element to the power source and has a first position where the indication element is not energized and a second position where the indication element is energized. An adequate force applied to the head and an at least partially translucent package body moves the switch to the second position. The package body has a first face and a second face. The first face and/or the second face have a rugose area configured to facilitate application of a force to the head and/or neck through the package body to place the switch in the second position.

9 Claims, 20 Drawing Sheets

(51) Int. Cl.

| | | |
|---|---|---|
| *A61C 17/34* | (2006.01) | |
| *B65D 81/00* | (2006.01) | |
| *B65D 75/32* | (2006.01) | |
| A61C 19/02 | (2006.01) | |
| B65D 75/36 | (2006.01) | |
| A46B 15/00 | (2006.01) | |

(52) U.S. Cl.
CPC ....... *A46B 15/0036* (2013.01); *A46B 15/0044* (2013.01); *A46B 2200/1066* (2013.01); *A61C 19/02* (2013.01); *A61C 2202/00* (2013.01); *B65D 75/366* (2013.01); *B65D 2203/12* (2013.01)

(58) Field of Classification Search
USPC .............. 206/361, 209, 209.1; 15/105, 22.1, 15/167.1; 248/560; 446/75, 72, 73; D9/415, 418
See application file for complete search history.

(56) References Cited

U.S. PATENT DOCUMENTS

| | | | | |
|---|---|---|---|---|
| 3,437,199 | A * | 4/1969 | Jacobson | B65D 75/366 206/470 |
| 3,907,193 | A * | 9/1975 | Heller | B29C 53/063 229/930 |
| 4,106,621 | A * | 8/1978 | Sorenson | 206/365 |
| 4,223,788 | A * | 9/1980 | Jaeger | B65D 75/366 16/352 |
| 4,236,652 | A * | 12/1980 | Beguhn | 222/92 |
| 4,680,825 | A * | 7/1987 | White | A46B 15/0002 116/202 |
| 4,680,925 | A * | 7/1987 | Bischofberger et al. | 57/263 |
| 4,829,621 | A * | 5/1989 | Phenegar | A46B 5/0075 15/144.1 |
| 4,925,025 | A * | 5/1990 | Anten et al. | 206/335 |
| 4,938,462 | A * | 7/1990 | Gould | 206/470 |
| 5,052,071 | A * | 10/1991 | Halm | 15/167.1 |
| 5,146,645 | A * | 9/1992 | Dirksing | A46B 5/0062 15/143.1 |
| 5,154,293 | A * | 10/1992 | Gould | B65D 75/366 206/461 |
| 5,188,222 | A * | 2/1993 | Pierce | 206/756 |
| D336,374 | S * | 6/1993 | Crawford | D4/199 |
| D338,123 | S * | 8/1993 | Crawford | D4/199 |
| 5,315,732 | A * | 5/1994 | Huefner | A46B 5/0062 15/143.1 |
| 5,375,711 | A * | 12/1994 | Bree et al. | 206/362.2 |
| 5,493,747 | A * | 2/1996 | Inakagata et al. | 15/22.1 |
| 5,494,252 | A | 2/1996 | Amit et al. | |
| 5,613,609 | A * | 3/1997 | Hamilton et al. | 206/531 |
| 5,718,335 | A * | 2/1998 | Boudreaux | 206/461 |
| 5,769,245 | A * | 6/1998 | Butler | 211/65 |
| 5,784,742 | A * | 7/1998 | Giuliani | A46B 15/0002 15/167.1 |
| 5,850,659 | A * | 12/1998 | Butler | A45D 44/18 15/167.1 |
| D405,531 | S * | 2/1999 | Bonds | D24/197 |
| 5,876,207 | A * | 3/1999 | Sundius | A46B 15/0012 15/105 |
| 6,126,008 | A * | 10/2000 | Cox | 206/471 |
| 6,189,693 | B1 | 2/2001 | Blaustein et al. | |
| 6,301,814 | B1 * | 10/2001 | Baxter | 40/429 |
| 6,311,837 | B1 * | 11/2001 | Blaustein | B65D 75/36 15/28 |
| 6,311,839 | B1 * | 11/2001 | Lo | 206/371 |
| 6,327,734 | B1 * | 12/2001 | Meginniss et al. | 15/105 |
| 6,389,636 | B1 * | 5/2002 | Savill | A46B 15/0002 116/212 |
| 6,412,137 | B1 * | 7/2002 | Heidari | A46B 9/12 15/105 |
| 6,668,416 | B1 * | 12/2003 | Georgi | A46B 5/007 15/167.1 |
| 6,889,829 | B2 | 5/2005 | Lev et al. | |
| 6,935,515 | B1 * | 8/2005 | Sookoo | 211/65 |
| 6,942,097 | B1 * | 9/2005 | Stremple et al. | 206/457 |
| 6,945,397 | B2 | 9/2005 | Brattesani et al. | |
| 6,954,961 | B2 | 10/2005 | Ferber et al. | |
| 7,059,471 | B2 | 6/2006 | Fattori | |
| 7,094,981 | B2 | 8/2006 | Sorrentino et al. | |
| 7,258,229 | B2 | 8/2007 | Chan | |
| D568,052 | S * | 5/2008 | Taylor et al. | D4/199 |
| 7,392,906 | B2 * | 7/2008 | Yu | 206/471 |
| 7,398,879 | B2 * | 7/2008 | Nottingham et al. | 206/349 |
| 7,413,080 | B2 * | 8/2008 | Van House | B65D 75/52 206/45.2 |
| 7,416,081 | B2 | 8/2008 | Sorrentino et al. | |
| 7,475,775 | B2 | 1/2009 | Fattori | |
| 7,513,369 | B1 * | 4/2009 | Lee | 206/779 |
| 8,016,129 | B2 * | 9/2011 | Peterson | 211/65 |
| 8,348,059 | B2 * | 1/2013 | Rice | 206/461 |
| 8,397,910 | B2 * | 3/2013 | Jimenez et al. | 206/362.2 |
| 8,485,360 | B2 * | 7/2013 | Teys et al. | 206/469 |
| 8,544,131 | B2 * | 10/2013 | Braun et al. | 15/22.1 |
| 8,904,590 | B2 * | 12/2014 | Jungnickel | A46B 15/0002 15/105 |
| 9,289,055 | B2 * | 3/2016 | Slocum | A46B 15/0038 |
| 9,505,540 | B2 * | 11/2016 | Nguyen | B65D 75/367 |
| 2004/0128780 | A1 * | 7/2004 | Chan | 15/22.1 |
| 2005/0066461 | A1 * | 3/2005 | Chang | A46B 15/0002 15/105 |
| 2005/0145519 | A1 * | 7/2005 | Fattori | B65D 25/20 206/361 |
| 2005/0161313 | A1 * | 7/2005 | Sorrentino | A61C 17/221 200/332 |
| 2006/0191810 | A1 * | 8/2006 | Chan | A61C 17/22 206/361 |
| 2007/0119736 | A1 * | 5/2007 | Kayser | A46B 5/0075 206/362.2 |
| 2008/0148507 | A1 * | 6/2008 | Kniese | A46B 5/0062 15/167.1 |
| 2008/0178401 | A1 * | 7/2008 | Claire-Zimmet | A46B 5/002 15/22.2 |
| 2008/0276398 | A1 * | 11/2008 | Nanda | A46B 15/0002 15/167.1 |
| 2009/0144920 | A1 * | 6/2009 | Nanda | A46B 15/0002 15/105 |
| 2009/0236241 | A1 * | 9/2009 | Jimenez | A61C 17/221 206/63.5 |
| 2010/0293731 | A1 * | 11/2010 | Stief | A46B 15/0002 15/106 |
| 2010/0325828 | A1 * | 12/2010 | Braun | A46B 15/0002 15/167.1 |
| 2011/0232012 | A1 * | 9/2011 | Nanda | A46B 15/0002 15/22.1 |
| 2012/0110763 | A1 * | 5/2012 | Jungnickel | A46B 5/0062 15/105 |
| 2012/0145567 | A1 * | 6/2012 | Nguyen | 206/63.5 |
| 2013/0087479 | A1 * | 4/2013 | Bloch et al. | 206/769 |
| 2013/0247321 | A1 * | 9/2013 | Sichau | 15/167.1 |
| 2013/0248388 | A1 * | 9/2013 | Jimenez | A46B 15/0085 206/214 |
| 2014/0083885 | A1 * | 3/2014 | Lee | B65D 75/32 206/361 |
| 2014/0231295 | A1 * | 8/2014 | Ponzini | B65B 5/04 206/462 |
| 2014/0339111 | A1 * | 11/2014 | Moskovich | B65D 75/366 206/362.3 |
| 2015/0282603 | A1 * | 10/2015 | Jimenez | A46B 11/0065 132/311 |
| 2015/0327668 | A1 * | 11/2015 | Bloch | A46B 15/0012 15/22.1 |
| 2016/0192769 | A1 * | 7/2016 | Bloch | A46B 15/0012 15/22.1 |
| 2016/0207683 | A1 * | 7/2016 | Moskovich | B65D 75/366 |
| 2016/0331119 | A1 * | 11/2016 | Schaefer | A46B 15/0012 |
| 2016/0331120 | A1 * | 11/2016 | Scheele | A46B 15/0012 |

* cited by examiner

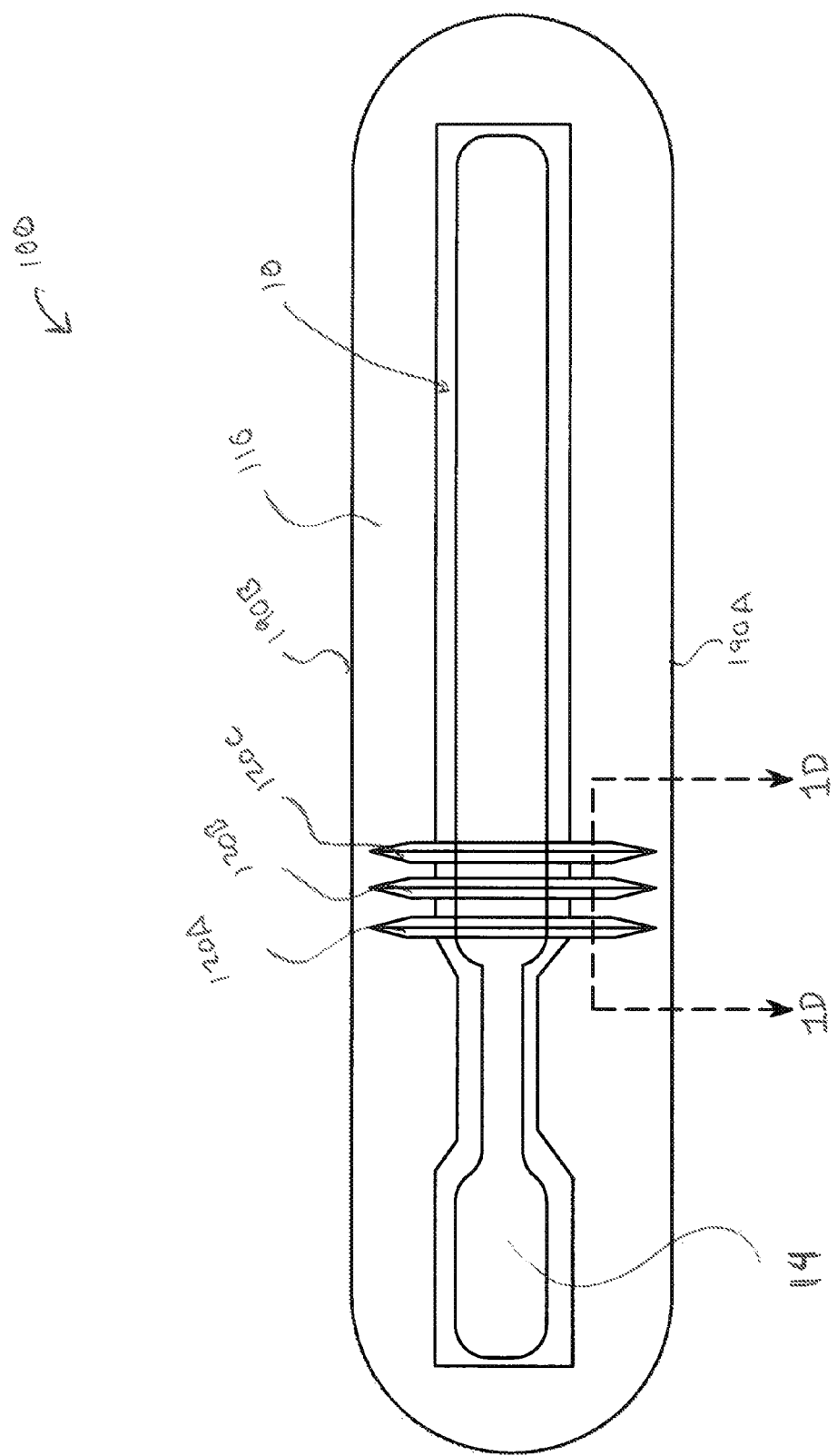

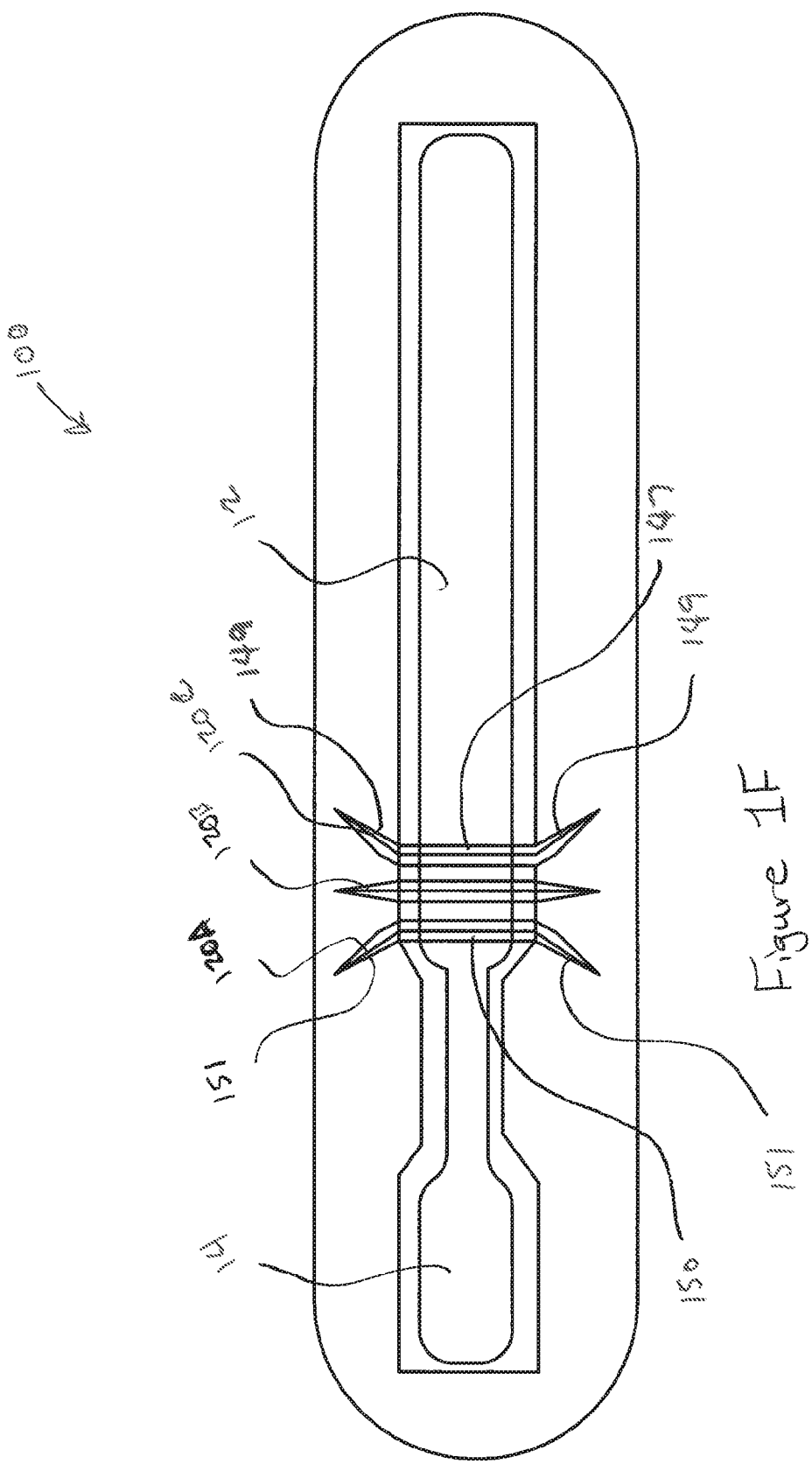

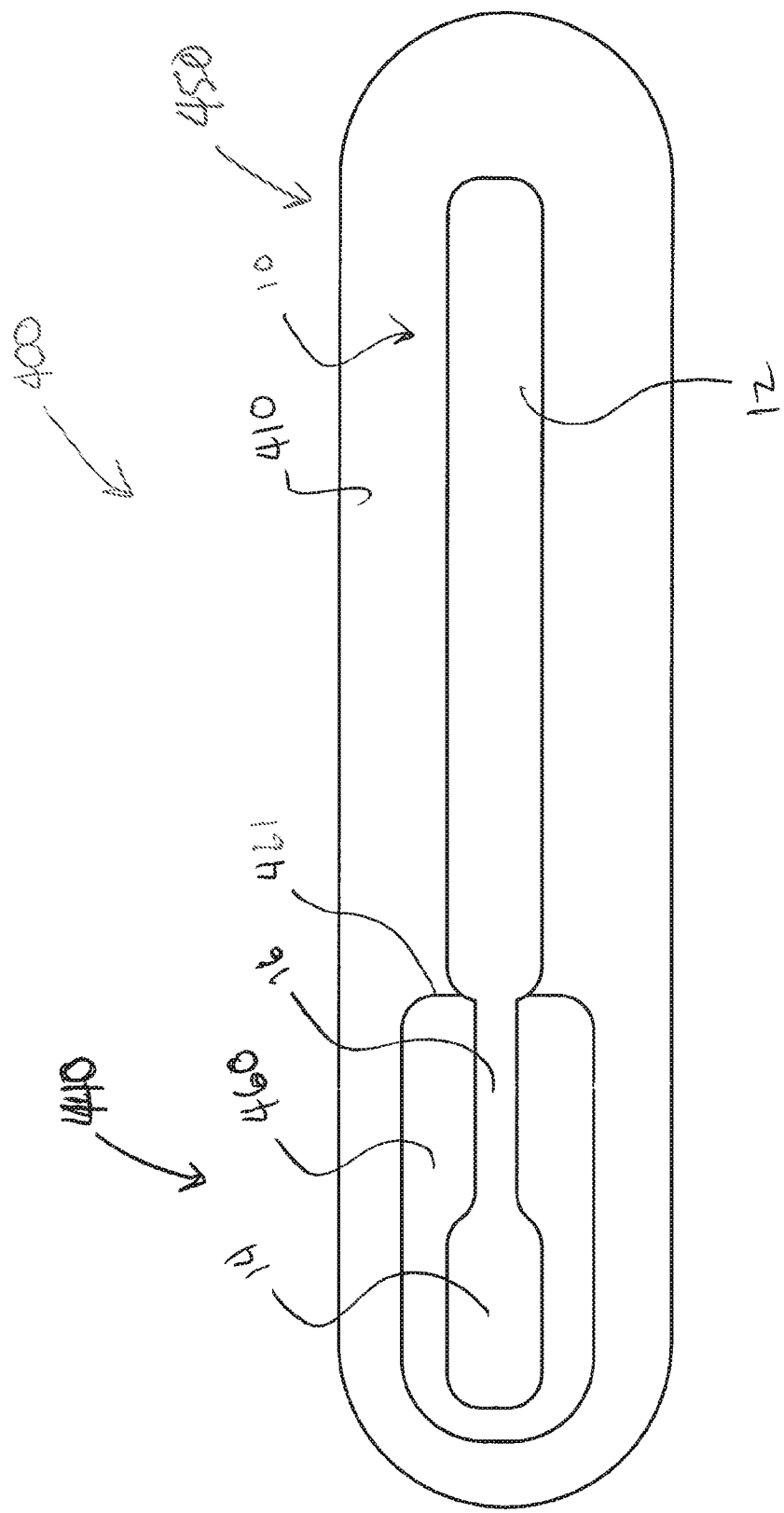

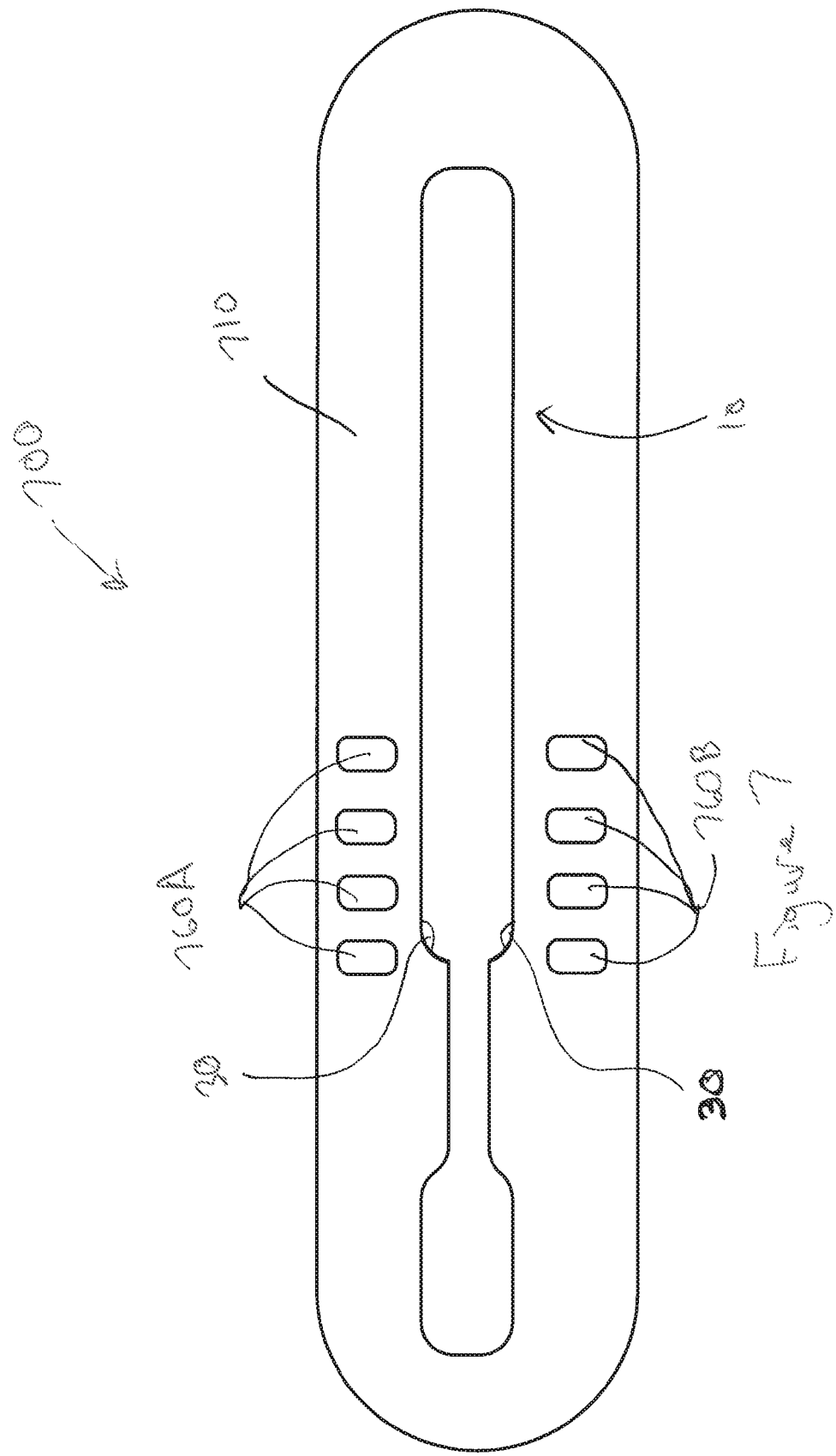

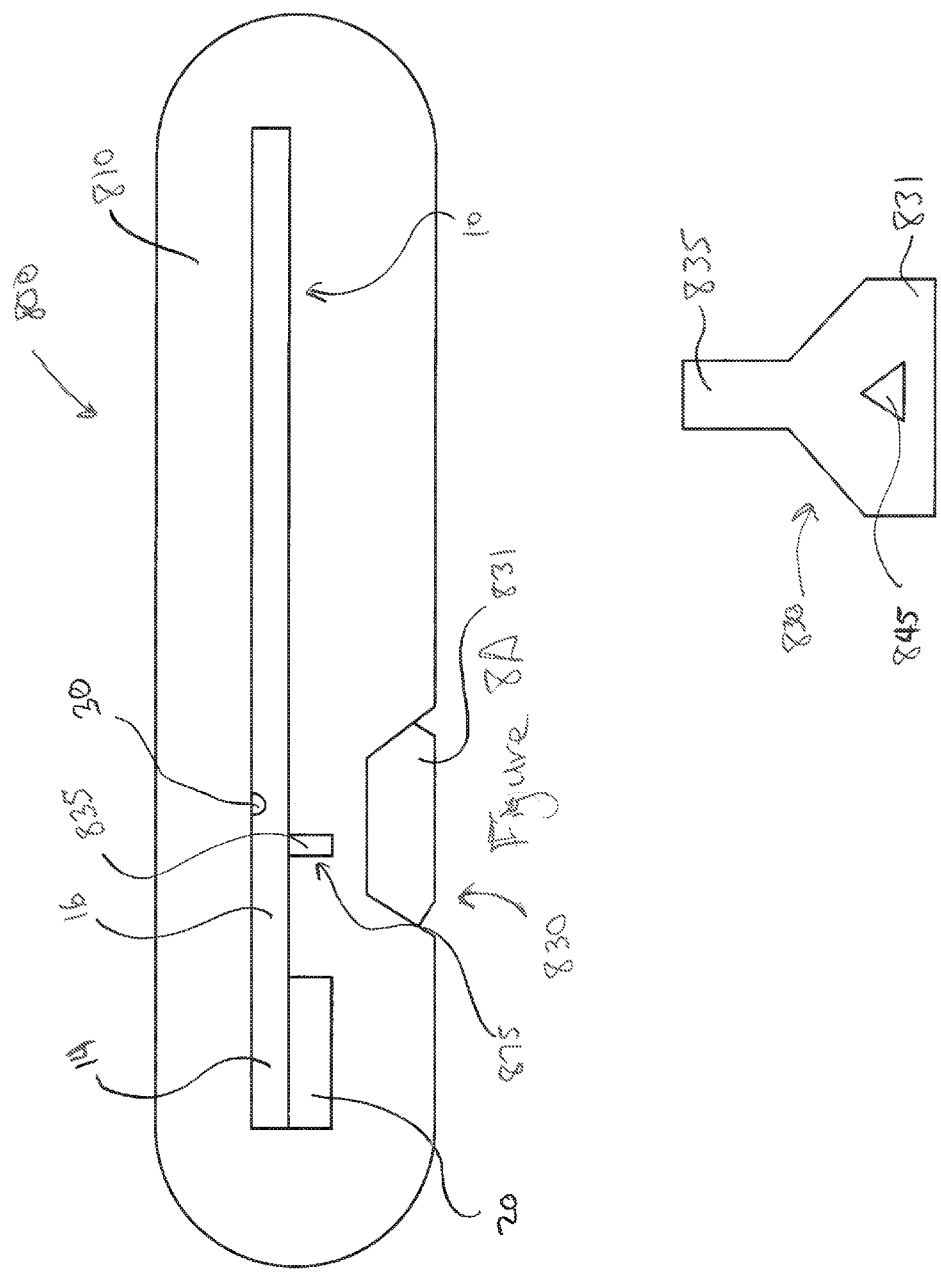

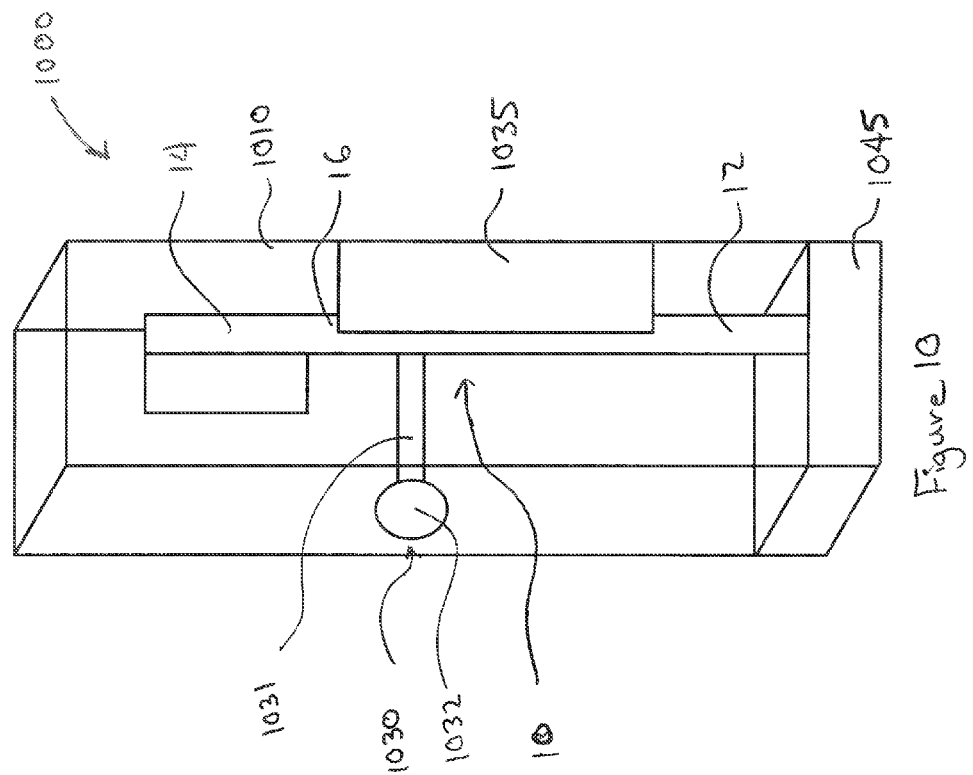

ORAL CARE INSTRUMENT AND PACKAGE THEREFORE

FIELD OF THE INVENTION

The present invention pertains to a personal hygiene device, more particularly to a personal hygiene device including a force indication system and a package therefore.

BACKGROUND OF THE INVENTION

The utilization of toothbrushes to clean one's teeth has long been known. During the brushing process, a user generally applies a force to the brush which is applied against the teeth and gums by the cleaning elements of the toothbrush. A minimum level of force must be applied to remove plaque and debris; however, high levels of force may have negative health consequences for an individual. For example, issues such as gum irritation, or over periods of time, gum recession or tooth enamel abrasion may occur. Unfortunately, the presence of these issues may exacerbate a contributing factor to the issues, i.e. high brushing force. Because some users may feel that these issues stem from poor cleaning, in an effort to correct the issues the users may apply even more force during brushing which in turn may cause more gum irritation and/or gum recession or tooth enamel abrasion.

In order to avoid or mitigate these issues, dental professionals may recommend the use of a soft bristled toothbrush. However, the use of a soft bristled toothbrush does not preclude the application of high brushing forces to the oral cavity. Furthermore, it is extremely difficult for an individual, when brushing, to determine the optimal force required for cleaning. While a user may apply a minimum level of force to enable cleaning, feeling the level at which the force is too high is difficult. In addition, studies have shown that the cleaning ability of a toothbrush may in fact be reduced if brushing force is increased to too high a level.

There are currently brushes on the market which provide feedback to the user regarding the application of too much pressure during brushing. However, without the ability to test these products on shelf, the consumer may purchase one of these available toothbrushes and realize only after the purchase that the feedback provided is insufficient or not desired.

Accordingly, a need exists for a personal hygiene implement which signals to the user when too high a brushing force is being applied which is in packaging which allows the user to test the brush on the store shelf.

SUMMARY OF THE INVENTION

A toothbrush in a display package, comprising: a handle; a head including a plurality of contact elements, the head being attached to a neck, the neck being disposed between the head and the handle and the neck being attached to the handle; an indication element disposed between the head and the handle, the indication element being in electrical communication with a power source; a switch for connecting the indication element to the power source, the switch having a first position in which the indication element is not energized and a second position for effecting the energizing of the indication element, the switch being placed in the second position when a force is applied to the head; and an at least partially translucent package body configured to at least partially cover the toothbrush, the package body including a first face and a second face, the first face and/or the second face having a rugose area configured to facilitate application of a force to the head and/or neck through the package body to place the switch in the second position.

A toothbrush in a display package, comprising: a handle; a head including a plurality of contact elements, the head being attached to a neck, the neck being disposed between the head and the handle and the neck being attached to the handle; an indication element disposed between the head and the handle, the indication element being in electrical communication with a power source; a switch for connecting the indication element to the power source, the switch having a first position in which the indication element is not energized and a second position for effecting the energizing of the indication element, the switch being placed in the second position when a force is applied to the head; and an at least partially translucent package body configured to at least partially cover the toothbrush, the package body having a first surface and a second surface opposite the first surface, wherein the package body has an opening extending through the package body from the first surface to the second surface, the opening being configured to facilitate application of a force to the head and/or neck through the package body to place the switch in the second position.

A toothbrush in a display package, comprising: a handle; a head including a plurality of contact elements, the head being attached to a neck, the neck being disposed between the head and the handle and the neck being attached to the handle; an indication element disposed between the head and the handle, the indication element being in electrical communication with a power source; a switch for connecting the indication element to the power source, the switch having a first position in which the indication element is not energized and a second position for effecting the energizing of the indication element, the switch being placed in the second position when a force is applied to the head; and an at least partially translucent package body configured to at least partially cover the toothbrush, the package body having a first surface and a second surface opposite the first surface, wherein the package body has a manipulation element having a control portion and a contact portion, the control portion being accessible to a consumer from outside the package body, and the contact portion being operatively connected to the toothbrush, wherein the manipulation element is to facilitate application of a force to the toothbrush to place the switch in the second position.

BRIEF DESCRIPTION OF THE DRAWINGS

It is to be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The embodiments set forth in the drawings are illustrative in nature and not intended to be limiting of the subject matter defined by the claims. The drawings illustrate various embodiments described herein, and together with the description serve to explain the principles and operations of the claimed subject matter.

FIG. 1C is a plan view showing the package of FIG. 1A.

FIG. 1F is a plan view showing an alternative embodiment of the package of FIG. 1A.

FIG. 4A is a plan view showing another embodiment for a package containing a personal hygiene article.

FIG. 7 is a plan view showing another embodiment for a package containing a personal hygiene article.

FIG. 8A is a plan view showing another embodiment for a package containing a personal hygiene article.

FIG. 8B is close up view of a manipulation element removed from the package of FIG. 8A for ease of viewing.

FIG. 10 is a perspective view showing another embodiment for a package containing a personal hygiene article.

DETAILED DESCRIPTION OF THE INVENTION

Definitions

Figure 1A:
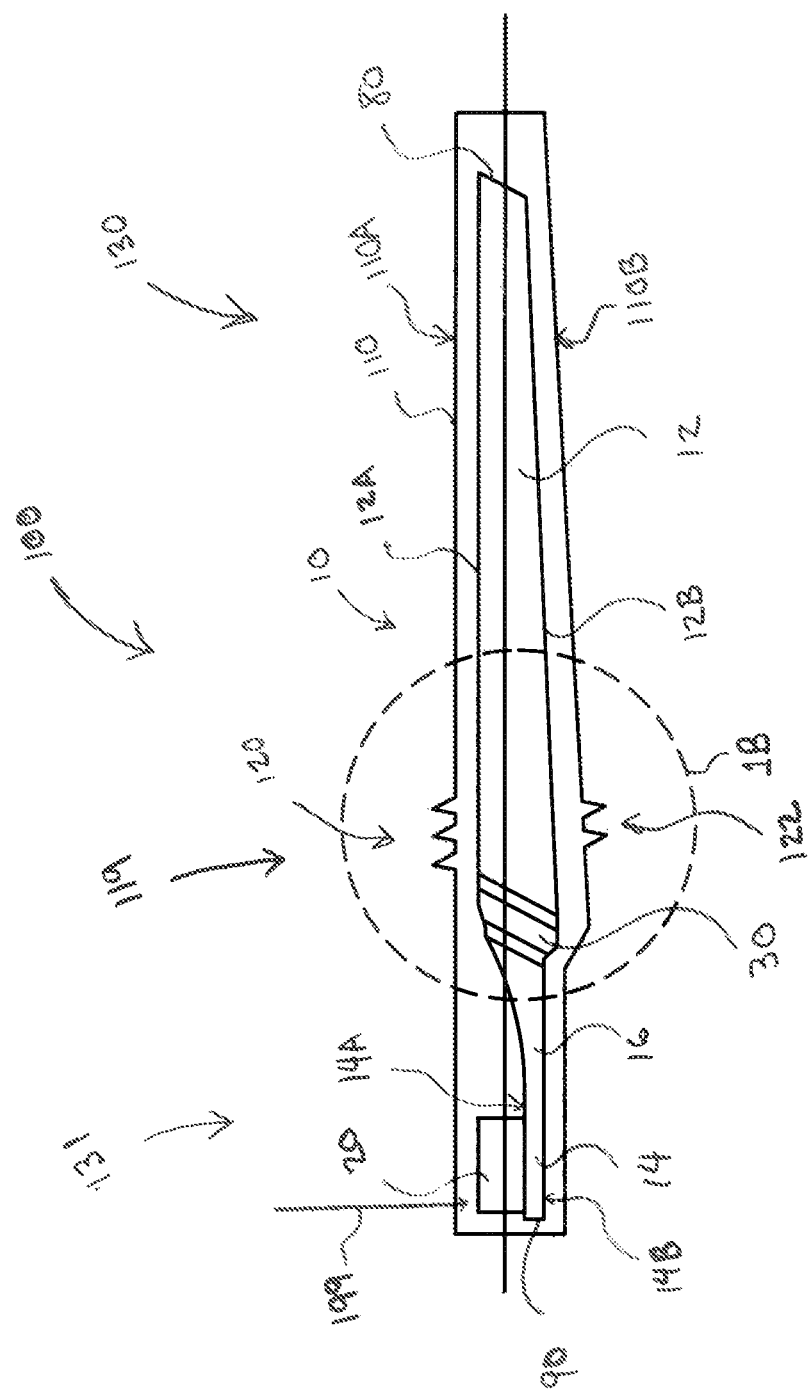
FIG. 1A is an elevation view showing an embodiment for a package containing a personal hygiene article.

The following text sets forth a broad description of numerous different embodiments of the present invention. The description is to be construed as exemplary only and does not describe every possible embodiment since describing every possible embodiment would be impractical, if not impossible, and it will be understood that any feature, characteristic, component, composition, ingredient, product, step or methodology described herein can be deleted, combined with or substituted for, in whole or part, any other feature, characteristic, component, composition, ingredient, product, step or methodology described herein. Numerous alternative embodiments could be implemented, using either current technology or technology developed after the filing date of this patent, which would still fall within the scope of the claims.

It should also be understood that, unless a term is expressly defined in this patent using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). No term is intended to be essential to the present invention unless so stated. To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. §112, sixth paragraph.

As used herein "longitudinal axis" refers to an axis for the display package which extends generally parallel to the long dimension of the toothbrush within the display package.

As used herein "lateral axis" refers to an axis for the display package which is generally perpendicular to the longitudinal axis and is generally parallel to a face of the display package.

As used herein "transverse axis" refers to an axis for the display package that is generally perpendicular to the longitudinal axis and the lateral axis.

As used herein "personal hygiene implement" refers to any implement which can be utilized for the purposes of personal hygiene. Some suitable examples include toothbrushes, either manual or powered; razors, either manual or powered; shavers, either manual or powered; trimmers, etc.

As used herein, "oral hygiene implement" refers to any device which can be utilized for the purposes of oral hygiene. Some suitable examples of such devices include toothbrushes (both manual and power), flossers (both manual and power), water picks, and the like.

Description:

For ease of explanation, the oral hygiene implement described hereafter shall be a manual toothbrush; however, as stated above, an oral hygiene implement constructed in accordance with the present invention is not limited to a manual toothbrush construction. Additionally, the packaging embodiments described hereafter are equally applicable to blades, razors, other personal hygiene implements, or the like.

The packaging described herein can allow a consumer to test the visual indication provided by a toothbrush without removal of the toothbrush from the package. For example, for the toothbrushes that provide a visible indication to the user that too much brushing force is being applied, a consumer can trigger the visible indication while the toothbrush is in the package via an application force which simulates a brushing force. The triggering of the visible indication can provide the consumer with some insight as to whether the visible indication is adequate and also provide some insight to the user on the functionality of the toothbrush.

There several types of packaging platforms which can be utilized for the display packages of the present invention. One example is a blister pack. The blister pack comprises a laminated structure which includes an at least partially transparent/translucent blister. The blister is attached to a backer. The blister comprises a cavity which receives the toothbrush such that the toothbrush is positioned between the blister and the backer.

Another example is a clamshell pack. The clamshell pack comprises a laminated structure similar to the blister pack. However, the clamshell pack comprises a front blister which is at least partially transparent and/or translucent and a back blister which may similarly be at least partially transparent and/or translucent. Both the front blister and the back blister have a portion of a cavity such that when combined, the cavity portions form the entire cavity in which the toothbrush resides. Additional packaging platforms are described hereafter.

As shown in FIG. 1A, a display package 100 may comprise a toothbrush 10 and a package body 110. The toothbrush comprises a handle 12, a head 14, and a neck 16 extending between the handle 12 and the head 14. A contact element field 20 extends from a first surface 14A of the head 14. The toothbrush 10 may comprise a distal end 80 and a proximal end 90. A tongue cleaner, soft tissue cleanser, massaging element, or the like, may be disposed on a second surface 14B of the head 14. The contact element field 20, the tongue cleaners, soft tissue cleansers, massaging elements, or the like, are discussed hereafter.

An indication element 30 may be disposed between the handle 12 and the head 14. The indication element 30 may provide a visible signal to a user for at least one of a plurality of conditions. For example, the visible signal may be provided when a user has brushed for an adequate amount of time, e.g. two minutes, when the toothbrush needs to be replaced, and/or when the user is applying too much force when brushing.

The handle 12 may comprise a power supply which is in electrical communication with the indication element 30. A switch may be positioned between the power supply and the indication element 30 such that in a non-use condition, the switch is in a first position which is open such that the indication element 30 is not supplied power from the power supply. In contrast, when a force 199 is applied to the head 14 and/or neck 16 is experienced by the toothbrush 10 exceeds a threshold value, the switch may move to a second position. In the second position, the switch may close thereby allowing power from the power supply to the indication element 30.

The package body 110 which covers the toothbrush 10, at least in part, may be, at least in part, translucent and/or transparent. The package body 110 may comprise a flexible portion 119 and a non-flexible portion(s) 130, 131. As shown, the flexible portion 119 may be disposed between the non-flexible portions 130 (adjacent the distal end 80 of the toothbrush 10) and 131 (adjacent the proximal end 90 of the toothbrush 10).

The package body 110 may comprise a first face 110A and a second face 110B. As shown, the first face 110A and the second face 110B within the location of the flexible portion 119 may each comprise a rugose area 120, 122. The rugose area(s) 120, 122 may facilitate the application of a force to the head 14 and/or neck 16 through the package body 110 to place the switch in the second position thereby energizing the indication element 30. Embodiments are contemplated where the first face 110A comprises the rugose area, e.g. the first rugose area 120 and the second face 110B does not comprise a rugose area. Embodiments are contemplated where the second face 110B comprises the rugose area, e.g. the second rugose area 122 and the first face 110A does not comprise a rugose area. The flexible portion 119 may comprise the rugose area(s) while the non-flexible portions may not comprise rugose area(s).

The placement of the rugose area, the number of ridges in the rugose area depends largely on the position of the brush within the package body 100. For example, if the brush is primarily positioned within a cavity in the first face 110A, then the second face 110B may not require a rugose area. Alternatively, where the brush is primarily positioned within a cavity in the second face 110B, then the first face 110A may not require a rugose area.

Figure 1B:
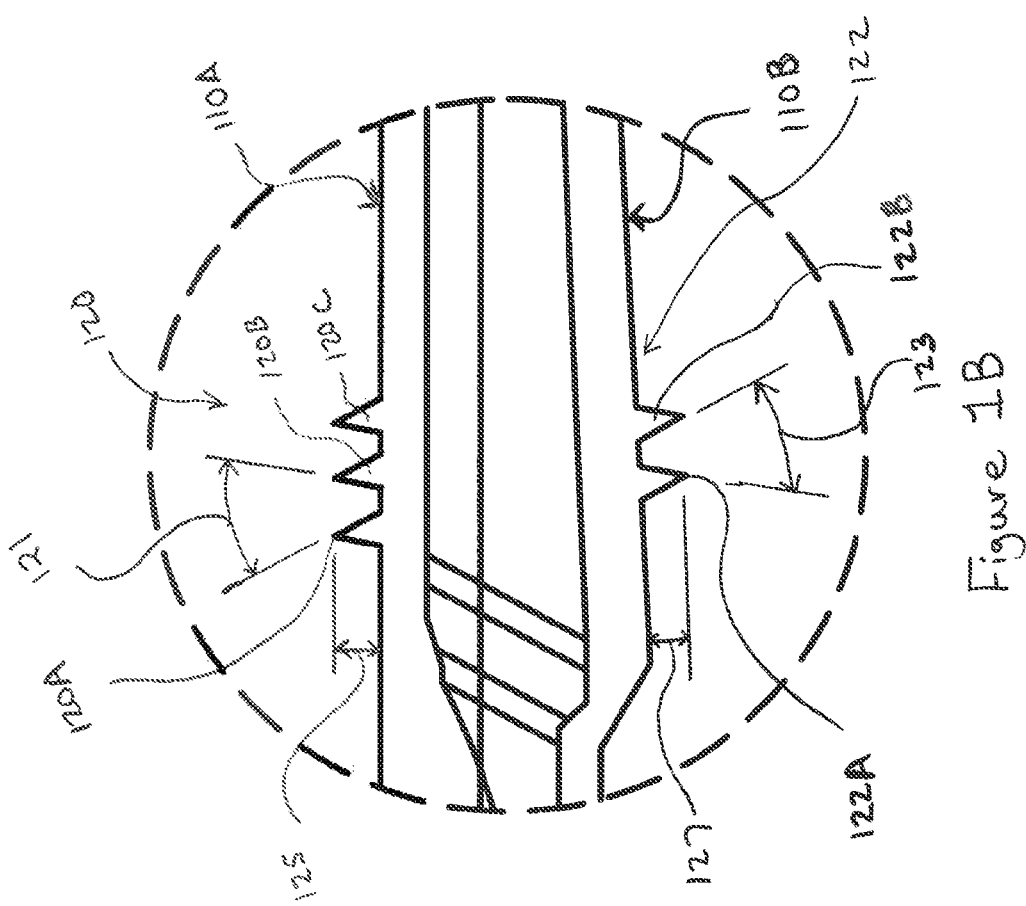
FIG. 1B is close up view of the package shown in FIG. 1A.

As shown in FIG. 1B, the first rugose area 120 may comprise a plurality of ridges 120A, 120B, and 120C. The ridges 120A, 120B, 120C may have adjacent faces which are angled from each other at a first angle 121. The first angle 121 may be about 60 degrees. Any suitable angle may be utilized. For example, the first angle 121 in some embodiments may be between about 0 and about 100 degrees. In some embodiments, the first angle 121 may be greater than about 0 degrees, greater than about 10 degrees, greater than about 15 degrees, greater than about 20 degrees, greater than about 25 degrees, greater than about 30 degrees, greater than about 40 degrees, greater than about 50 degrees, greater than about 60 degrees, greater than about 70 degrees, greater than about 80 degrees, greater than about 90 degrees, less than about 100 degrees, less than about 90 degrees, less than about 80 degrees, less than about 70 degrees, less than about 60 degrees, less than about 50 degrees, less than about 40 degrees, less than about 30 degrees, less than about 20 degrees, less than about 10 degrees, or any number or any range within the values provided.

The second face 110B may comprise the second rugose area 122 which comprises a plurality of ridges 122A and 122B. The ridges 122A and 122B may have adjacent faces which are angled from each other at a second angle 123. The second angle 123 may be less than the first angle 121. In some embodiments, the second angle 123 may be between about 0 degrees to about 100 degrees. The second angle 123 may have the values provided above as described with regard to the first angle 121.

Referring back to the first rugose area 120, the ridges 120A, 120B, and/or 120C, may have a first height 125 of about 2 mm. The first height 125 may be any suitable value. For example, the first height 125 may be between about 0.5 to 10 mm. In some embodiments, the first height 125 may be greater than about 0.5 mm, greater than about 1.0 mm, greater than about 1.5 mm, greater than about 2.0 mm, greater than about 3.0 mm, greater than about 4.0 mm, greater than about 5.0 mm, greater than about 6.0 mm, greater than about 7.0 mm, greater than about 8.0 mm, greater than about 9.0 mm, or less than about 10.0 mm, less than about 9.0 mm, less than about 8.0 mm, less than about 7.0 mm, less than about 6.0 mm, less than about 5.0 mm, less than about 4.0 mm, less than about 3.0 mm, less than about 2.0 mm, less than about 1.0 mm, or any number or range within the values provided.

Regarding the second rugose area 122, the ridges 122A and 122B may have a second height 127 of about 2 mm. The second height 127 may be any suitable value. For example, the second height 127 may be about 0.5 to about 10 mm. The second height 127 may have the same heights as described heretofore with regard to the first height 125.

As shown in FIG. 1B, the first rugose area 120 may comprise more ridges than the second rugose area 122. Additionally, the ridges of the first rugose area 120 may be longitudinally offset from the ridges in the second rugose area 122. As discussed previously, the inclusion of a rugose area may be dependent upon the depth of the cavity in the first face or second face. For those embodiments where the cavity in which the brush is placed is deep, additional ridges may be required to ensure that that portion of the package with the deep cavity has flexibility.

Referring to FIG. 1C, in some embodiments, one or more of the ridges 120A, 120B, 120C may extend in a lateral direction toward lateral edges 190A and 190B of the package body 110. The extension of the ridges 120A, 120B, and/or 120C may provide a visual cue to the consumer that the toothbrush 10 has some flexibility.

Figure 1D:
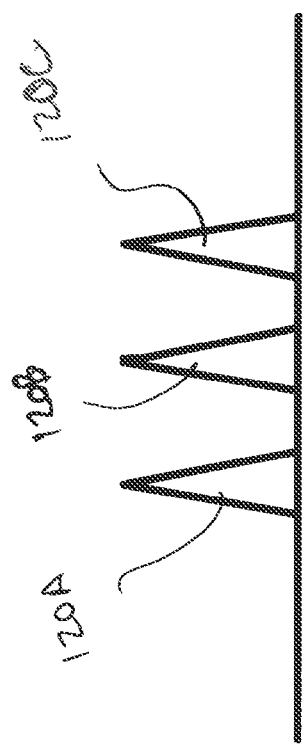
FIG. 1D is a partial cross section of the package of FIG. 1A as shown in FIG. 1C taken along line 1D-1D.
Figure 1E:
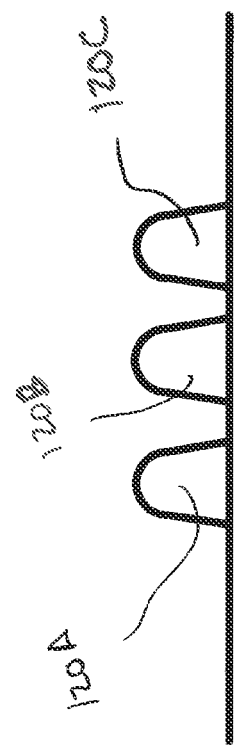
FIG. 1E is a partial cross section showing an alternative embodiment to that shown in FIG. 1D.

Referring to FIGS. 1D and 1E, the ridges 120A, 120B, 120C, may be configured in any suitable manner. For example, the ridges may comprise a triangular shape. In contrast, the ridges 120A, 120B, and/or 120C may comprise a non-standard shape. For example, instead of a narrow tip, the ridges 120A, 120B, and/or 120C may comprise a rounded tip. In some embodiments, the first face 120A and/or the second face 120B may be thermoformed. In such embodiments, the ridges may have a rounded tip. The rounded tip may ensure that during processing the mold over which the plastic is deformed does not punch through the plastic material.

As shown in FIG. 1F, the ridges 120A, 120B, and 120C, may be configured to provide a unique visual effect to the consumer. For example, the ridges 120A, 120B, and/or 120C, may comprise an offset end which is oriented toward the head 14 or toward the handle. As shown, the ridge 120A comprises offset ends 151 positioned on either side of a transverse portion 150. The offset ends 151 may be oriented toward the head 14. Additionally, as shown, the ridge 120C may comprise offset ends 149 positioned on either side of a transverse portion 147. The offset ends 149 may be oriented toward the handle 12. Although not shown, the ridge 120B may comprise an offset end, e.g 149, 151, or a plurality thereof. Additionally, embodiments are contemplated where at least one of the ridges 120A, 120B, and/or 120C comprises a plurality of offset ends which include an offset end 149 and an offset end 151.

Referring now to FIGS. 1A, 1B, and 1F, for those embodiments where the indication element 30 is positioned such that when energized in the display package 100, the indication element 30 provides a visible output through the second face 110B, the ridges 122A and/or 122B in the second rugose area 122 may be configured similar to the ridges 120A, 120B, and/or 120C, discussed above.

As discussed previously, embodiments are contemplated where the first face 110A and/or the second face 110B comprise a rugose area. For those embodiments which utilize a clamshell package platform, the first face 110A and/or the second face 110B may comprise a rugose area. In contrast, for those embodiments which utilize a blister package platform, the first face 110A may have a rugose area, while the second face 110B does not include a rugose area.

Figure 2:
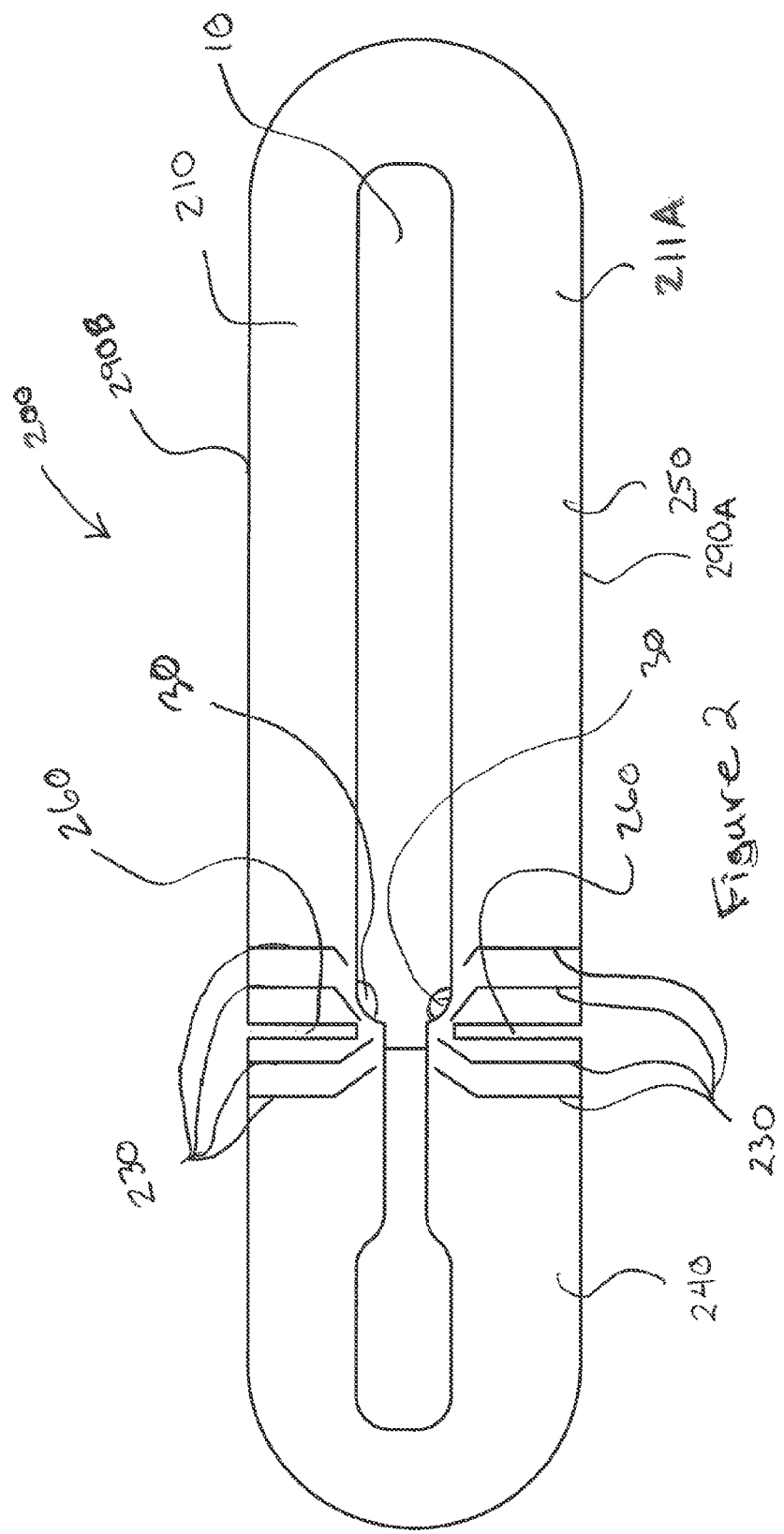
FIG. 2 is a plan view showing another embodiment for a package containing a personal hygiene article.

As shown in FIG. 2, a display package 200 may comprise a package body 210 and the toothbrush 10. The package body 210 encapsulates, at least in part, the toothbrush 10. The package body 210 includes a first portion 240 and a second portion 250. In between the first portion 240 and the second portion 250, the package body 210 may comprise a plurality of recesses 260 which, in some embodiments, may extend from lateral edge 290A inboard and from lateral edge 290B inboard. The package body 210 may additionally comprise a plurality of light channels 230 which transmit light from the indication element 30. The light channels 230 may extend to lateral edges 290A/290B of the display package 200 from adjacent the indication element 30.

The display package 200 may be configured such that a consumer can grasp the first portion 240 and the second portion 250 and bend either the first portion 240 or the second portion 250 with respect to the other. The bending of the display package 200 can simulate an applied brushing force which exceeds a first threshold thereby placing the switch in the second position, and therefore energizing the indication element 30. In embodiments where the indication element comprises a light source, e.g. LED, the light channels 230 can provide a unique visual perspective to the consumer.

Embodiments are contemplated where the display package 200 comprises light channels 230 on a first face 211A and/or on a second face opposite the first face 211A. For those embodiments where the indication element 30 is limited to providing visual indication through the second face, the light channels 230 on the second face can provide a unique visual effect for the consumer. The display package 200 can be realized by using either the blister package platform or the clamshell platform.

Figure 3:
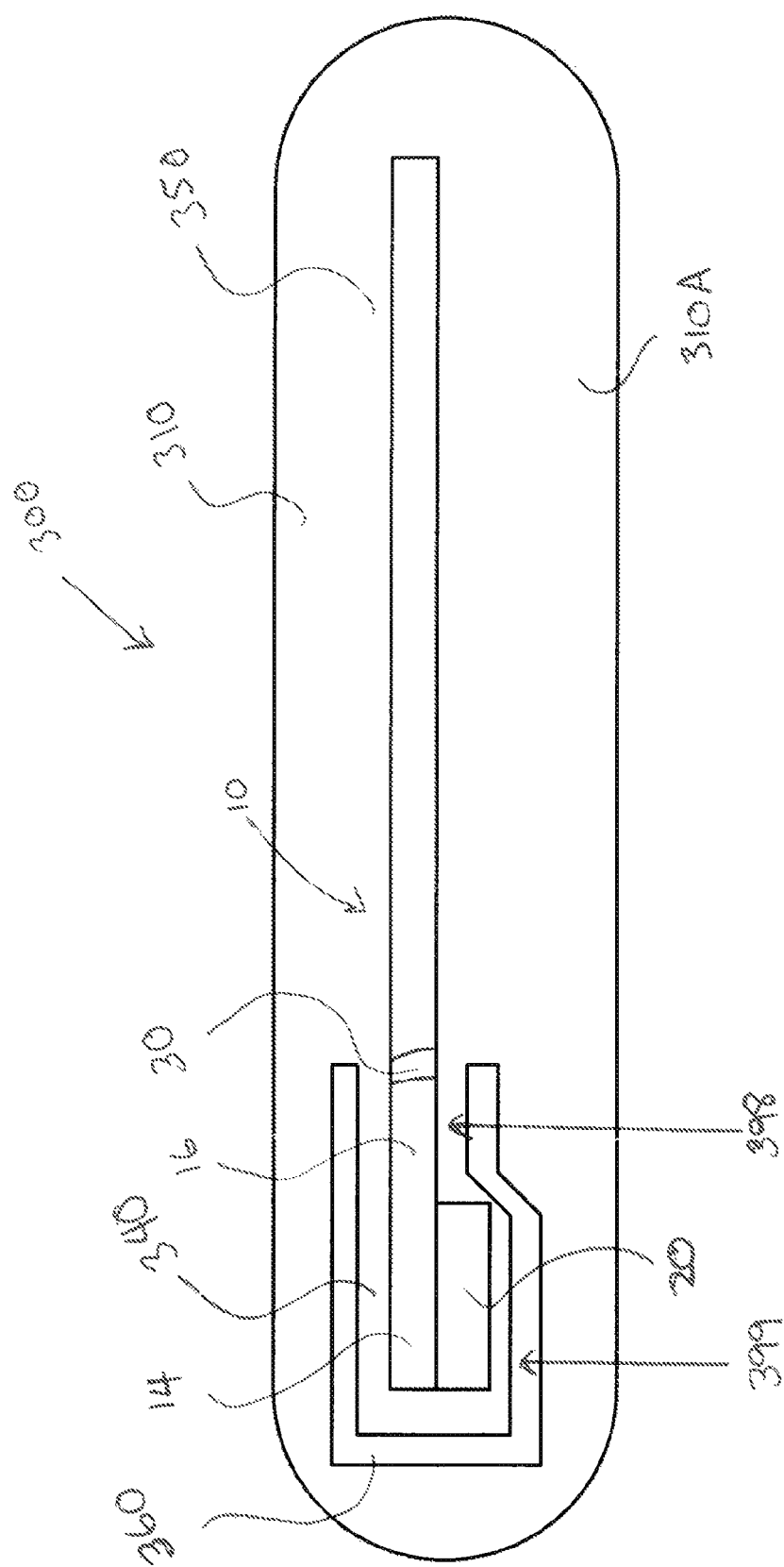
FIG. 3 is a plan view showing another embodiment for a package containing a personal hygiene article.

Referring to FIG. 3, a display package 300 may comprise a package body 310 which encapsulates, at least in part, the toothbrush 10 as described heretofore. The package body 310 comprises a first portion 340 and a second portion 350. The first portion 340 may be configured to flex, bend, with respect to the second portion 350. In order to move the switch to the second position, a user can apply a force 399 to the contact element field 20 of the toothbrush 10. Alternatively, or in conjunction with the force 399, a user can apply a force 398 to the neck 16 of the toothbrush 10. When the applied force 399 and/or 398, simulate an applied brushing force which exceeds a first threshold, then the switch is moved to the second position and the indication element 30 becomes energized.

As shown, the package body 310 may further comprise an opening 360 which, at least in part, surrounds the head 14 of the toothbrush 10. The opening 360 extends from a first face 310A through a second face opposite the first face 310A. The package body 310 may further comprise indicia providing visual indication to a consumer as to where the force should be applied that causes the switch to move to the second position. For example, in some embodiments, the package body 310 may comprise indicia adjacent the contact element field 20. In some embodiments, the package body 310 may comprise indicia adjacent the neck 16. In some embodiments, the package body 310 comprises indicia which indicate multiple sites upon which a force could be applied to move the switch to the second position. The display package 300 can be realized by using either the blister package platform or the clamshell platform.

Figure 4B:
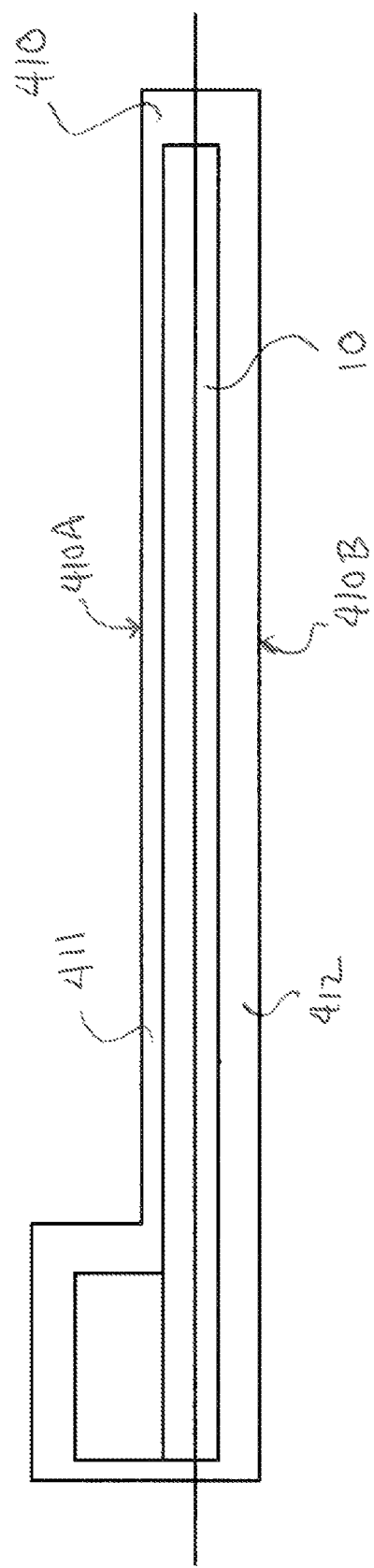
FIG. 4B is an elevation view showing the package of FIG. 4A.

Referring to FIGS. 4A and 4B, a display package 400 has a package body 410 which encapsulates, at least in part, the toothbrush 10. The package body 410 comprises an opening 460 adjacent the head 14, a first portion 450, and a second portion 440. The opening 460 is positioned in the second portion 440. The opening 460 can allow the head 14 and neck 16 pivot with respect to a portion of the package body 410. The handle 12 may be fixed within the package body 410 such that the handle 12 does not rotate with respect to the first portion 450 of the package body 410.

As shown, the package body 410 may comprise a first blister 411, a second blister 412, and an intermediate member 413 positioned between the first blister 411 and the second blister 412. The opening 460 may extend through the intermediate member 413 such that in the opening 460, the first blister 411 and the second blister 412 are joined to each other. Additionally, adjacent a first side 461 of the opening 460, the first blister 411 and/or the second blister 412 may comprise a built in fulcrum allowing the first blister 411 and/or the second blister 412 to bend with respect to the first portion 450.

The display package 400 can be realized by using either the blister package platform or the clamshell platform. However, with regard to the blister package platform, it is important to note that as shown in FIG. 4B, the first blister 411 and the second blister 412 may form a first surface 410A and a second surface 410B, opposite the first surface 410A, of the package body 410. In contrast, the backer, as described previously for the blister package platform, typically forms the equivalent of the second surface 410A.

Figure 5A:
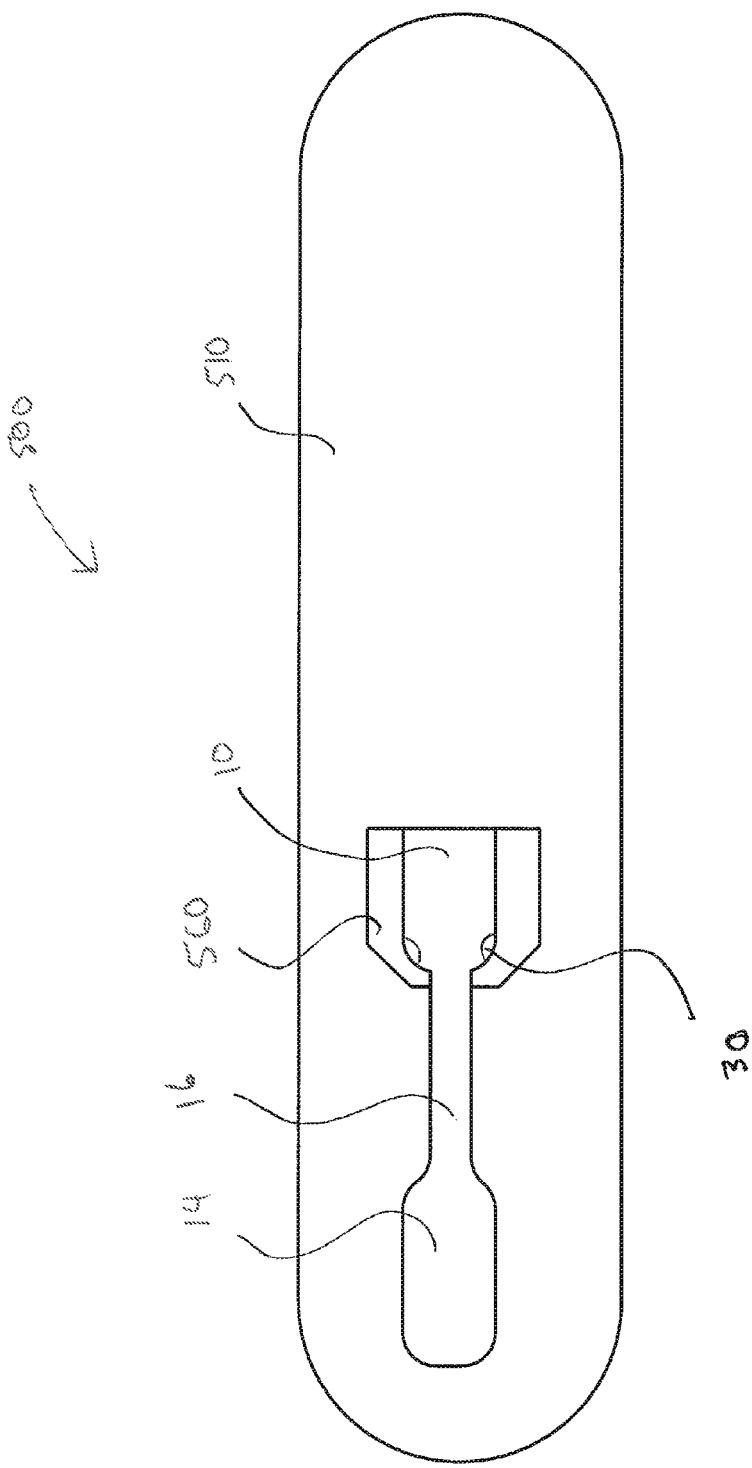
FIG. 5A is a plan view showing another embodiment for a package containing a personal hygiene article.
Figure 5B:
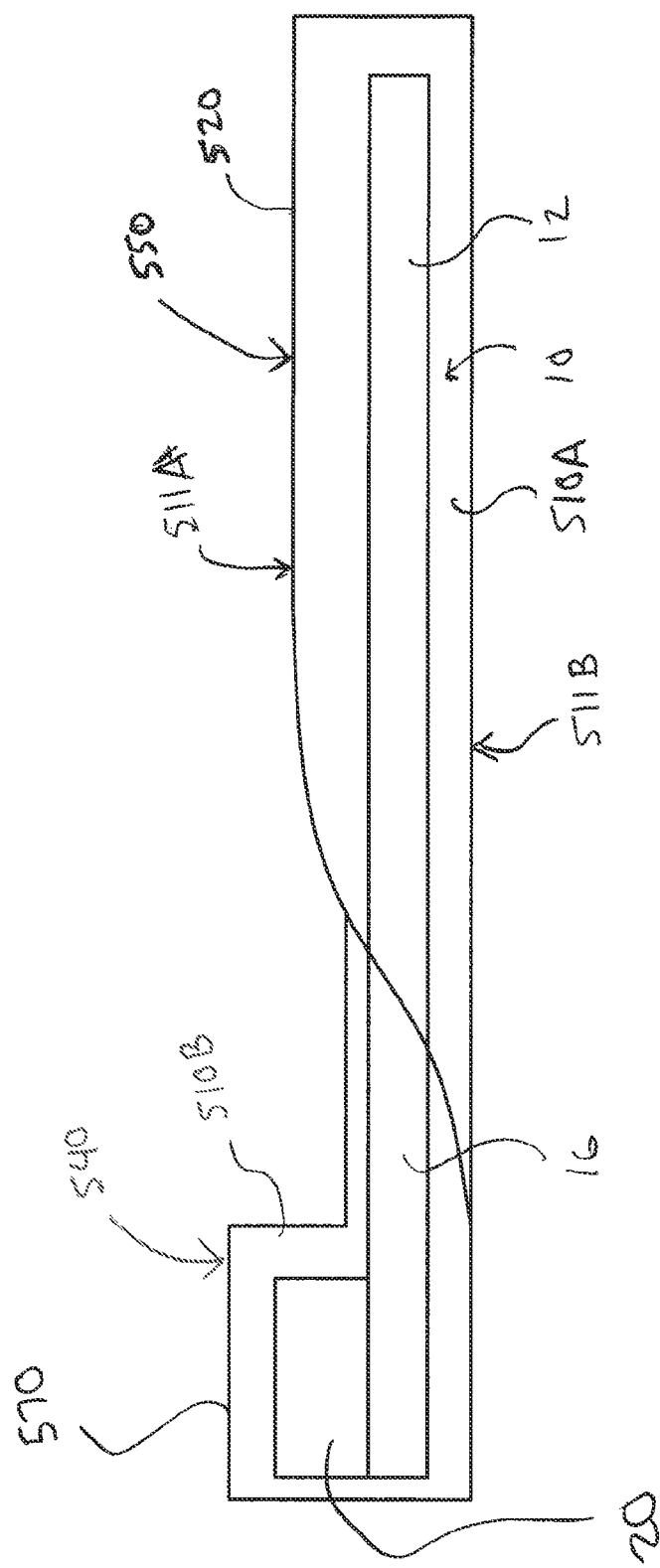
FIG. 5B is an elevation view showing the package of FIG. 5A.

In another embodiment, an opening may be positioned differently than shown in FIGS. 4A and 4B. As shown in FIGS. 5A and 5B, a display package 500 comprises a package body 510 that at least partially encapsulates the toothbrush 10. The package body 510 may comprise an opening 560 that is positioned near the indication element 30 of the toothbrush 10. The package body 510 has a first portion 550 and a second portion 540. The package body 510 may further comprise a first blister 510A, a second blister 510B, and a backer 520.

As shown, in the first portion 550, the backer 520 may form at least a portion of a front surface 511A which covers the handle 12 of the toothbrush 10. Opposite the front surface 511A, a back surface 511B may be formed by a first blister 510A. Between the first portion 550 and the second portion 540, the package body 510 may transition such that the front surface 511A, adjacent the opening 560, declines toward the back surface 511B. In doing so, a portion of the toothbrush 10 becomes visible to the consumer when viewing the front surface 511A.

In the second section 540, the front surface 511A may be formed by the backer 520 and by a second blister 510B. The decline of the first surface 511A toward the second surface 511B can allow the second portion 540 to bend with respect to the first portion 550, thereby allowing the consumer to move the switch to the second position to illuminate the indication element 30 within the package body 510.

In such embodiments, an application indicator 570 may be placed on the second blister 510B adjacent the contact elements 20. The application indicator 570 may provide visual indication to the consumer as to where the application of force should occur on the package body 510 in order to energize the indication element 30. In some embodiments, an application indicator may be placed adjacent the neck 16. In some embodiments, a plurality of application indicators may be provided. For example, the application indicator 570 as described above may be provided, and additionally, an application indicator positioned adjacent the neck 16 may be provided.

The display package 500 can be realized by using the blister package platform. The package can comprise rugose areas.

Figure 6:
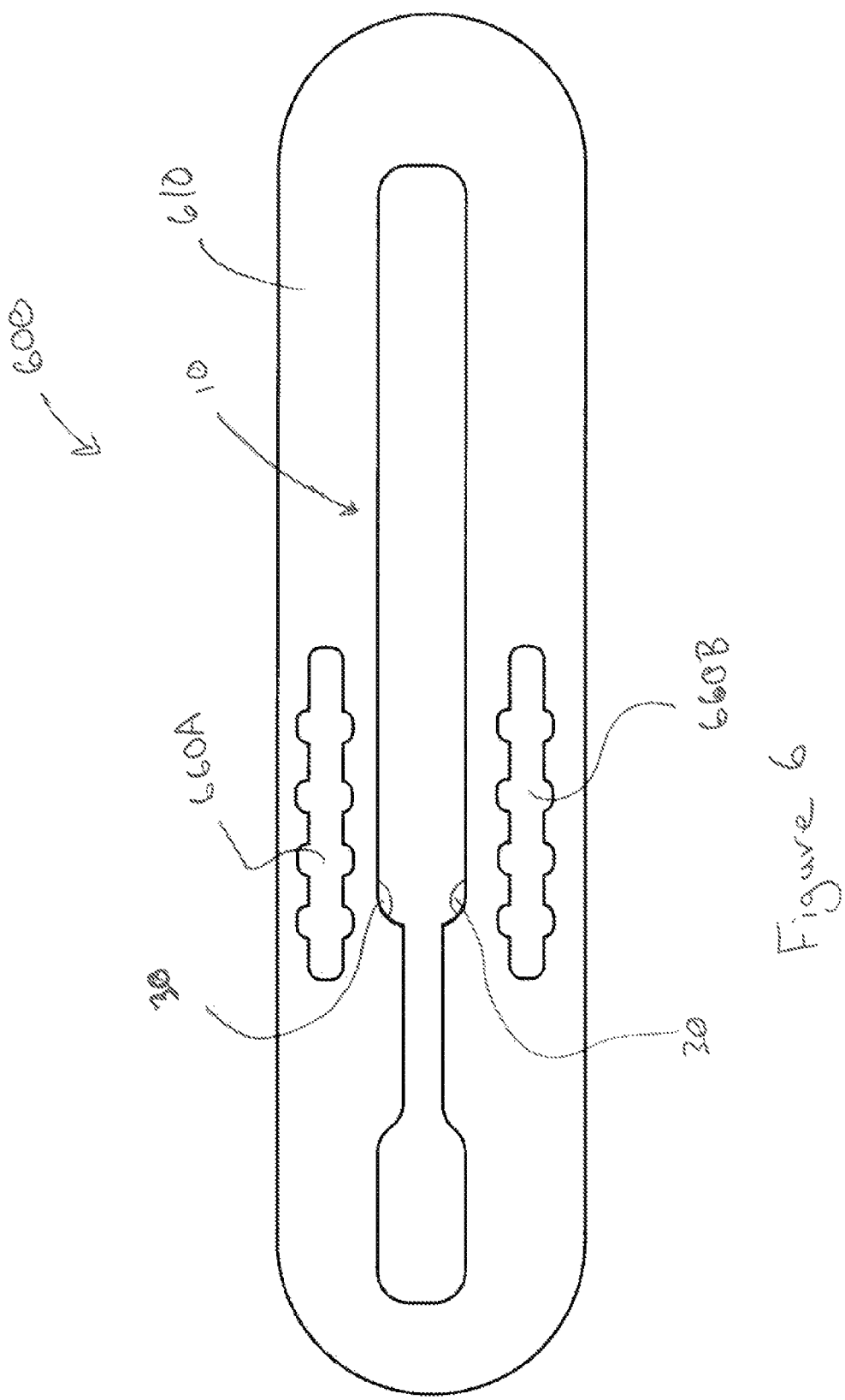
FIG. 6 is a plan view showing another embodiment for a package containing a personal hygiene article.

As shown in FIG. 6, a display package 600 may comprise a package body 610 which encapsulates, at least in part, the toothbrush 10. As shown, the package body 610 may comprise a plurality of openings 660A and 660B which are positioned on either side of the toothbrush 10 adjacent the indication element 30. The display package 600 can be realized by using either the blister package platform or the clamshell platform.

For those embodiments utilizing the blister pack platform, the openings 660A and 660B may extend through the blister and/or the backer. For those embodiments utilizing the clamshell pack platform, the openings 660A and 660B may extend through the first blister and/or the second blister.

The openings 660A and 660B may allow a second portion 640 of the package body 610 to bend with regard to a first portion 650 of the package body 610. Additionally, the openings 660A and 660B can provide visual indication to the consumer that the display package 600, including the package body 610 and the toothbrush 10 are flexible in nature.

The openings 660A and 660B may comprise any suitable shape. For example, as shown, the openings 660A and 660B may comprise zig-zags, circles, squares, rectangles, polygons, the like, and combinations thereof, which are either discrete or a plurality of such openings could be joined together to collectively form an opening.

As shown in FIG. 7, a display package 700 comprises a package body 710 encapsulating, at least in part, the toothbrush 10. The package body 710 may comprise a plurality of openings 760A and 760B which are positioned adjacent the indication element 30. As shown the openings 760A and 760B may comprise a plurality of discrete openings. As stated above the discrete openings may have any suitable shape.

Regarding FIGS. 8A and 8B, a display package 800 comprising a package body 810 which at least partially encapsulates the toothbrush 10 is shown. The package body 810 may comprise a blister which accommodates the toothbrush 10 and a backer. The backer may comprise a slot allowing for the movement of a manipulation element 830 with respect to the backer. The manipulation element 830 may be movably disposed within the slot.

The manipulation element 830 may be configured to move in a direction generally parallel to a transverse axis of the toothbrush, i.e. generally parallel with the long direction of the contact elements 20. The manipulation element 830 may comprise a control portion 831 and a contact portion 835. In operation, the consumer could activate the indication element 30 by moving the manipulation element 830 inward toward the neck 16. With the movement of the manipulation element 830 inward, the contact portion 835 makes contact with the neck 16, thereby applying a force to the neck 16. Once the applied force to the neck 16 exceeds that of a brushing threshold force, the switch moves to the second position, and the indication element 30 is energized.

As previously mentioned, the manipulation element 830 may be disposed within a slot in the backer. For example, the backer may comprise a laminate structure where the manipulation element 830 is positioned between layers of the backer. In such embodiments, the backer may comprise a window 875 which allows the consumer to view the control portion 835. In order to establish visual contrast, the backer may comprise a first color and the manipulation element 830 and/or the control portion 835 may comprise a second color which is different than the first color.

In other embodiments, the manipulation element 830 may comprise a gripping element 845 which can facilitate manipulation by the consumer. The gripping element 845 may comprise an indentation or a plurality of indentations in the control portion 831.

The display package 800 may utilize either the blister pack platform or the clamshell platform.

Figure 9A:
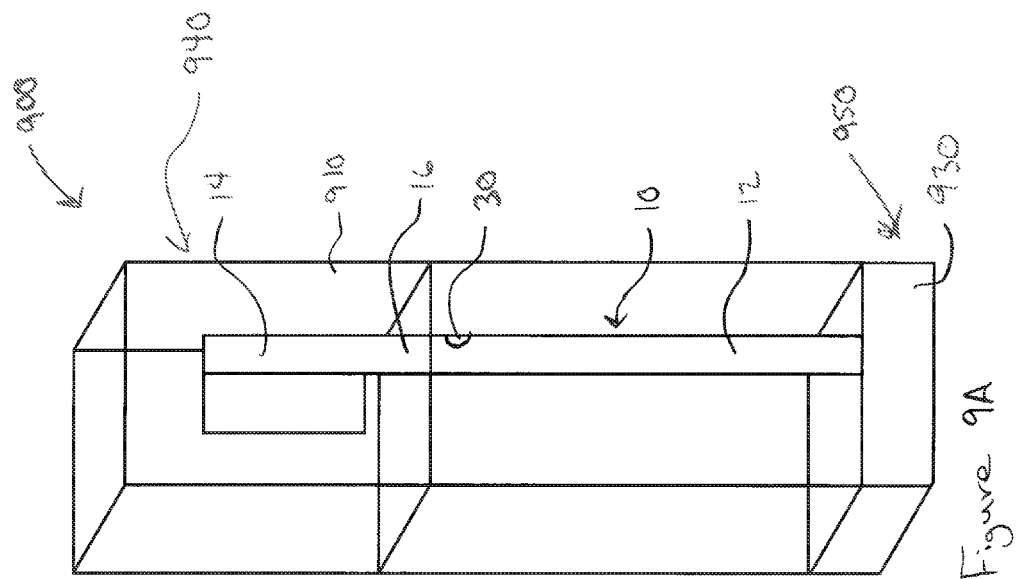
FIG. 9A is a perspective view showing another embodiment for a package containing a personal hygiene article.
Figure 9B:
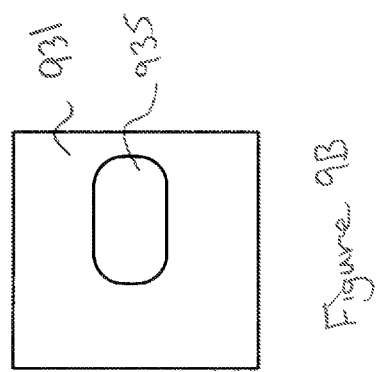
FIG. 9B is a plan view showing a plate removed from the package of FIG. 9A for ease of viewing.

Regarding FIGS. 9A and 9B, a display package 900 comprising a package body 910 which at least partially encapsulates the toothbrush 10 is shown. The package body 910 may comprise a stationary portion 940 and a movable portion 950. The movable portion 950 may comprise a dial 930 which can be rotated with respect to the stationary portion 940. Although not shown, the dial 930 may comprise a recess which can accommodate the distal end 80 of the toothbrush 10. The recess may be configured such that the toothbrush 10 is fixed with respect to the recess. In such embodiments, the rotation of the dial 930 causes the toothbrush 10 to rotate within the stationary portion 940.

The stationary portion 940 may comprise at least partially transparent/translucent wall(s). Additionally, an outer periphery of the stationary portion 940 may be polygonal.

However, in some embodiments, the outer periphery of the stationary portion 940 may be circular. The stationary portion 940 may further comprise a plate 931 which is disposed within the stationary portion 940. The toothbrush 10 may be positioned such that the neck 16 of the toothbrush 10 passes through an aperture 935 of the plate 931. When the switch is in the first position, i.e. the indication element 30 is not energized, the plate 931 does not exert a force on the neck 16 of the toothbrush 10. When the dial 30 is rotated with respect to the stationary portion 940, a boundary of the aperture 935 can apply a force to the neck 16 which exceeds a first threshold of brushing force thereby moving the switch to the second position and thereby energizing the indication element 30.

Regarding FIG. 10, a display package 1000 comprising a package body 1010 which at least partially encapsulates the toothbrush 10 is shown. The package body 1010 may comprise a manipulation element 1030 and a first support 1035 and a second support 1045. The manipulation element 1030 may comprise a control portion 1032 and a contact portion 1031. The contact portion 1031 may contact the neck 16 of the toothbrush 10, when the control portion 1032 is depressed by the consumer.

The first support 1035 may provide support to the toothbrush 10 such that during the application of a force via the contact portion 1030, rotation of the toothbrush 10 with respect to the package body 1010 is discouraged. The second support 1045 may provide additional support to discourage the movement and/or rotation of the toothbrush 10 with respect to the package. In operation, the consumer may depress the control portion 1032 which may cause the contact portion 1031 to engage the neck 16 of the toothbrush 10. If the application of force to the control portion 1032 exceeds a first threshold of brushing force, then the force applied to the neck 16 will cause the switch to move to the second position, thereby causing the indication element to be energized.

Figure 11A:
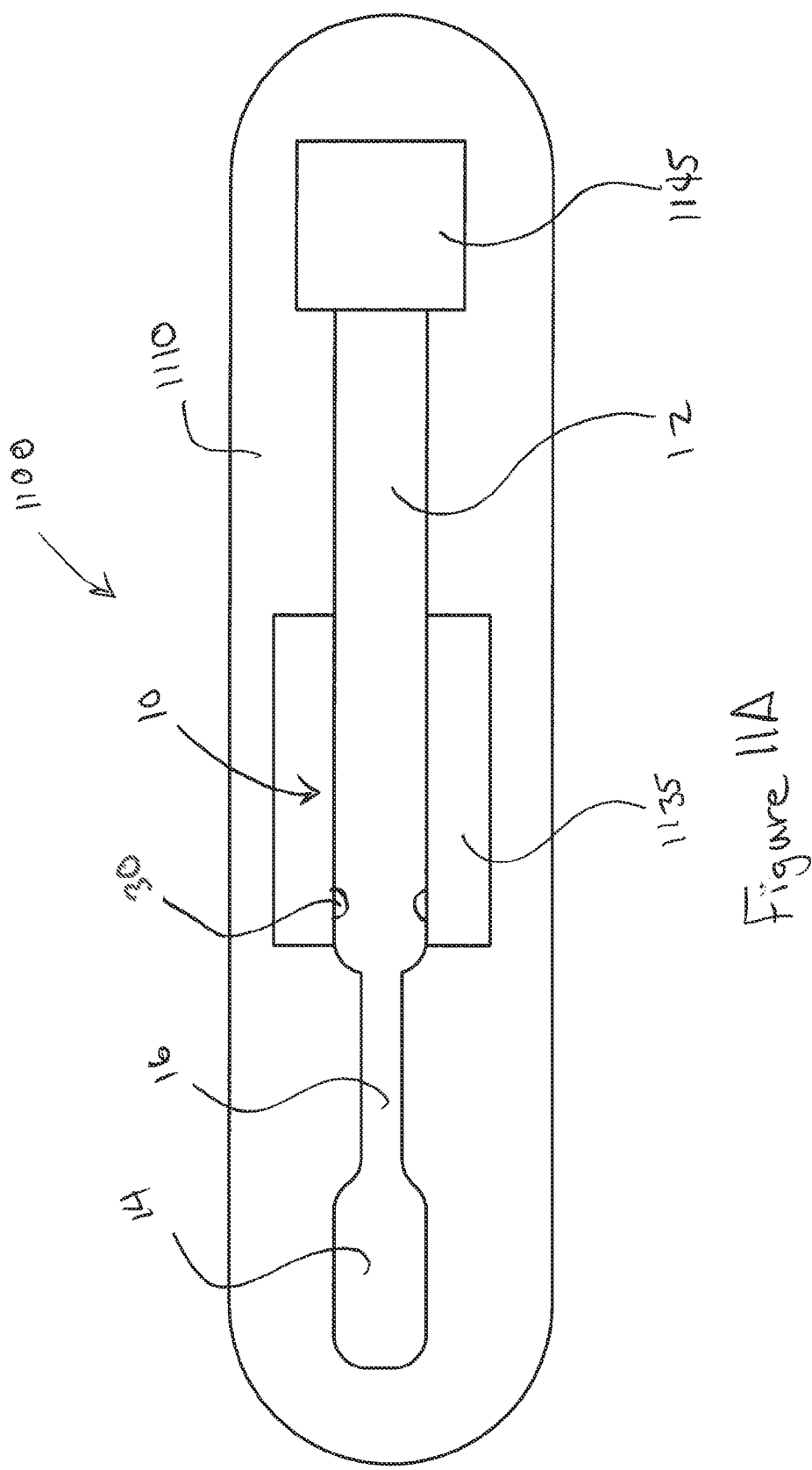
FIG. 11A is a plan view showing another embodiment for a package containing a personal hygiene article.
Figure 11B:
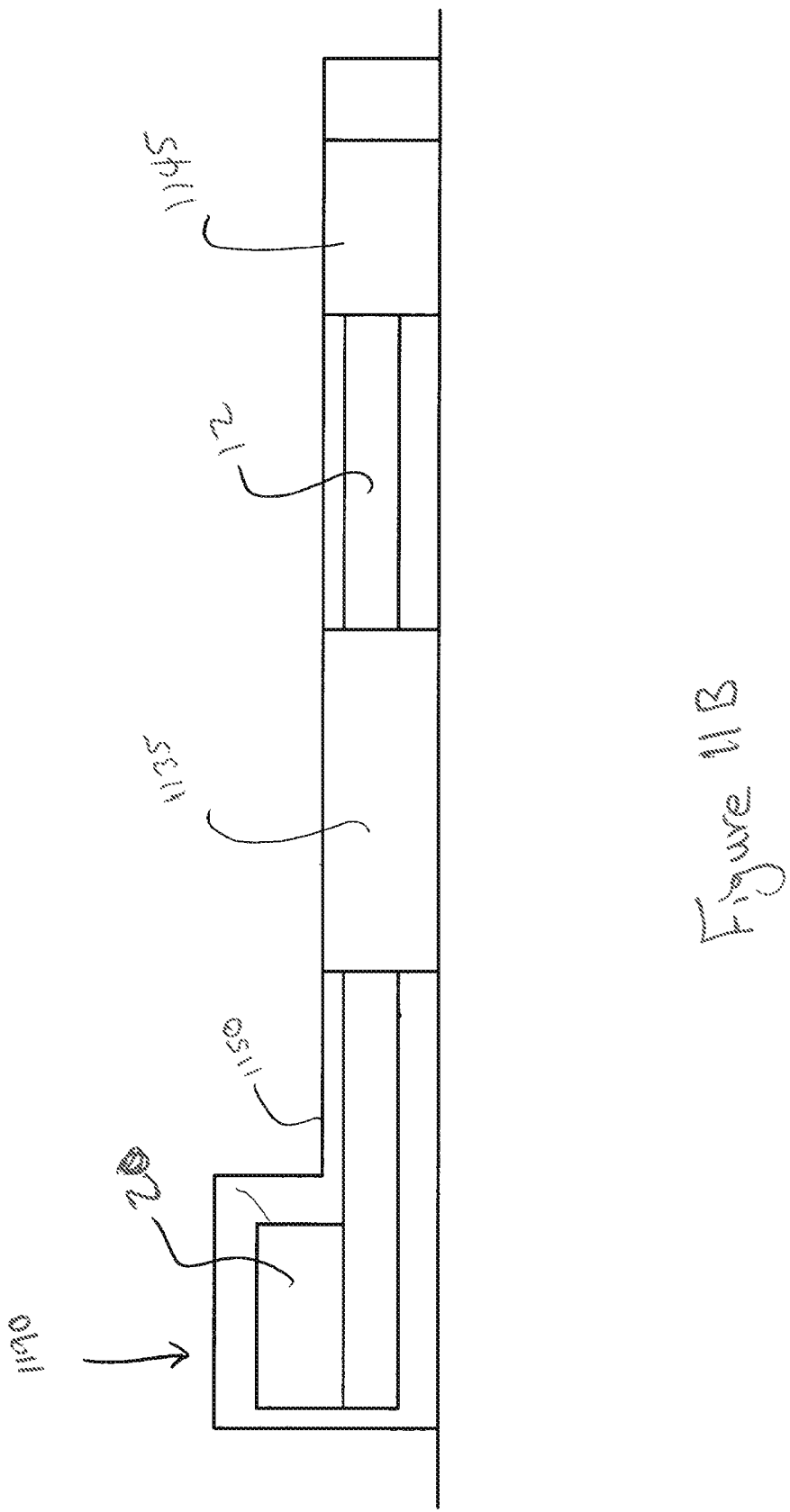
FIG. 11B is an elevation view showing the package of FIG. 11A.

Regarding FIGS. 11A and 11B, a display package 1100 comprising a package body 1110 which at least partially encapsulates the toothbrush 10 is shown. The package body 1110 may comprise a first support 1135 and a second support 1145. The first support 1135 may provide support to the toothbrush 10 such that during the application of a force to the neck 16 and/or the head 14, rotation of the toothbrush 10 with respect to the package body 1110 is discouraged. The second support 1145 may provide additional support to discourage the movement and/or rotation of the toothbrush 10 with respect to the package body 1110.

In operation, the consumer may apply a force 1190 to the head 14, neck 16, contact elements 20, or combinations thereof. If the applied force 1190 exceeds a first threshold of brushing force, then the switch moves to the second position, thereby causing the indication element to be energized.

The package body 1110 may further comprise indicia which provide a visual indication to the consumer as to where the applied force 1190 should be applied to the display package 1100. For example, the package body 1110 may comprise indicia positioned on a blister 1150 adjacent the contact elements 20. In other embodiments, indicia may be provided adjacent the neck 16 and/or the head 14. The display package 1100 may utilize either the blister pack platform or the clamshell platform. Additionally, in some embodiments, the display package 1100 may be shrink wrapped.

Figure 12:
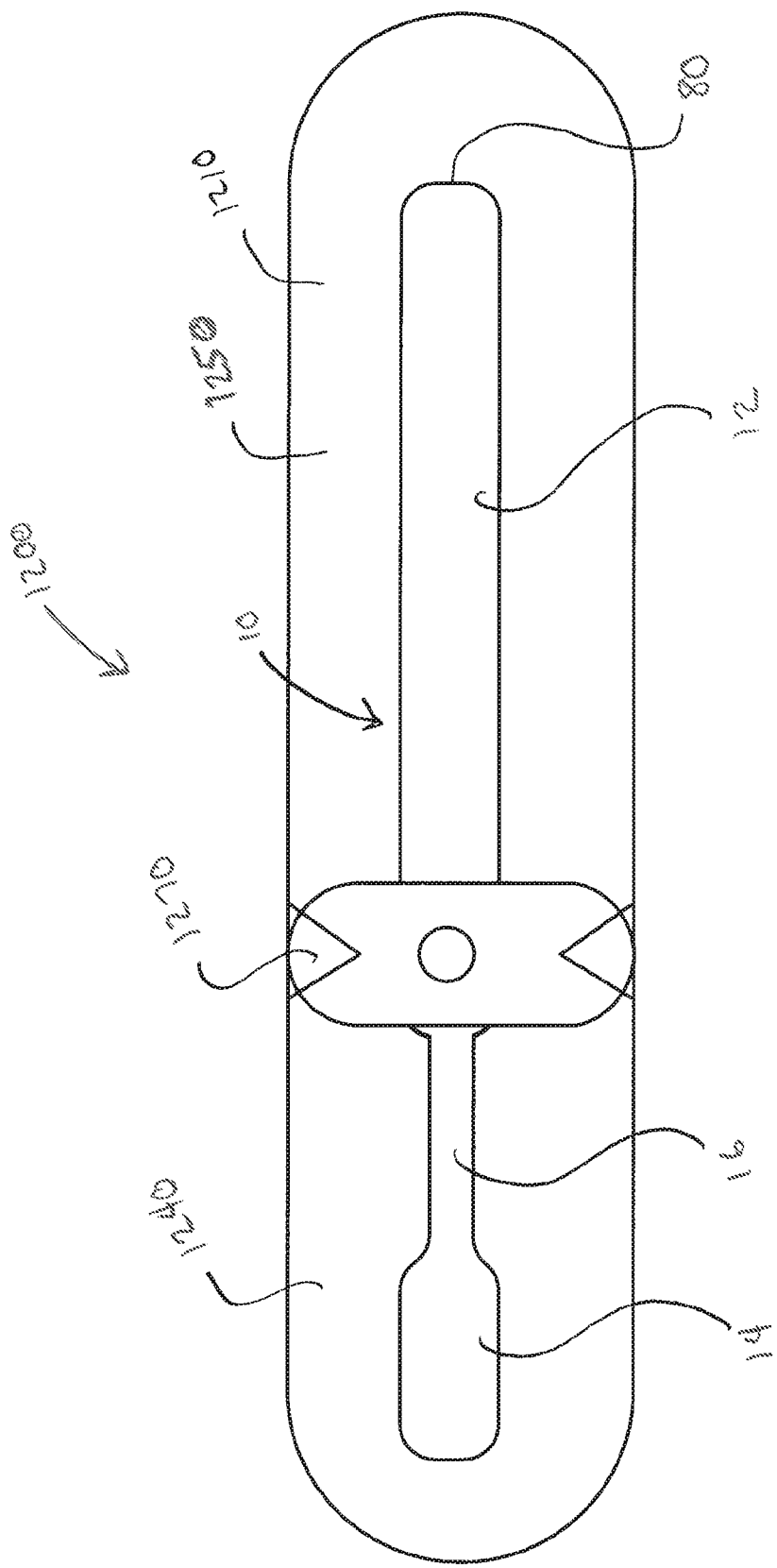
FIG. 12 is a plan view showing another embodiment for a package containing a personal hygiene article.

Referring to FIG. 12, a display package 1200 may comprise a package body 1210 which encapsulates, at least in part, the toothbrush 10. The package body 1210 may comprise a first portion 1250 and a second portion 1240. The package body 1210 may further comprise a joint section 1270 which allows the second portion 1240 to move with respect to the first portion 1250. In some embodiments, the second portion 1240 may pivot about an axis that is generally parallel to the lateral axis of the toothbrush 10. In other embodiments, the second portion 1240 may pivot about an axis that is generally parallel to the transverse axis of the toothbrush 10.

In operation, the consumer could pivot the second portion 1240 with respect to the first portion 1250 thereby moving the switch to the second position and thereby energizing the indication element 30. In order to discourage movement of the toothbrush 10 within the package body 1210 during the pivoting of the second portion 1240, the package body 1210 may further comprise a support which holds the distal end 80 of the toothbrush 10 in a fixed position.

The joint section 1270 may be disposed between the first portion 1250 and the second portion 1240. The joint section 1270 may be transparent and/or translucent, in part, such that when the indication element 30 is energized, the indication element 30 may be visible to the consumer holding the display package 1200.

Embodiments are contemplated where the toothbrush 10 faces the side, and the package is pivoted in the plane of the longitudinal axis. The display package 1200 may utilize the blister pack platform or the clamshell pack platform.

Figure 13:
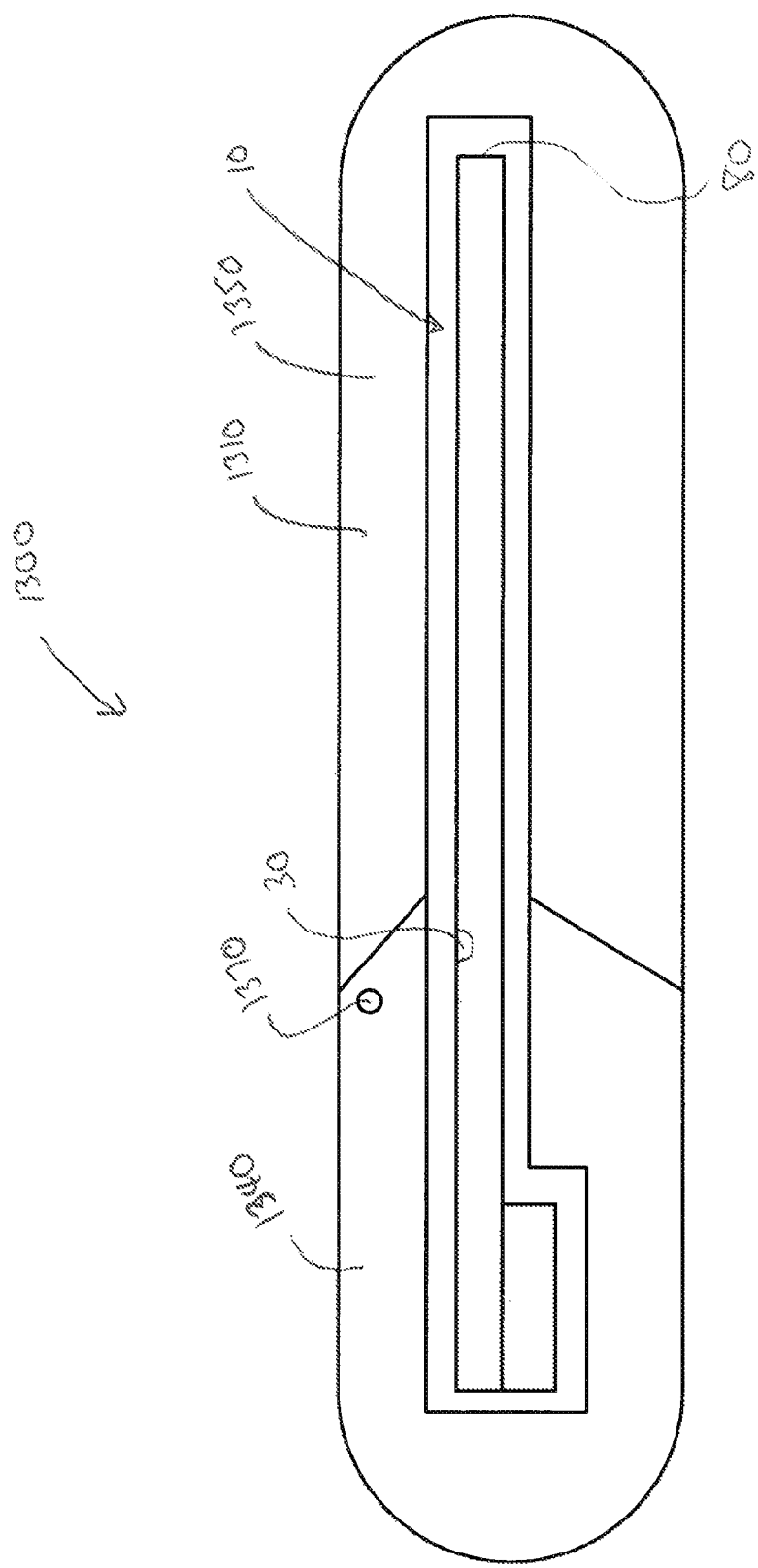
FIG. 13 is a plan view showing another embodiment for a package containing a personal hygiene article.

Referring to FIG. 13, a display package 1300 may comprise a package body 1310 which encapsulates, at least in part, the toothbrush 10. The package body 1310 may comprise a first portion 1350 and a second portion 1340. The package body 1310 may further comprise a pivot 1370 which allows the second section 1340 to pivot with respect to the first section 1350. As shown, the second portion 1340 may pivot about an axis which is generally parallel to the transverse axis of the toothbrush 10.

In operation, the consumer could pivot the second portion 1340 with respect to the first portion 1350 thereby moving the switch to the second position and thereby energizing the indication element 30. In order to discourage movement of the toothbrush 10 within the package body 1310 during the pivoting of the second portion 1340, the package body 1310 may further comprise a support which holds the distal end 80 of the toothbrush 10 in a fixed position.

The display package 1300 may utilize the blister pack platform or the clamshell pack platform.

For any of the embodiments described herein, mechanisms may be implemented which enhance the flexibility of the package body in addition to those descried for the specific embodiment. For example, rugose areas may be provided to increase flexibility for any of the embodiments described herein.

Referring back to FIG. 1A, the indication element 30 may be placed in any suitable location on the toothbrush 10. For example, in some embodiments, the indication element 30 may surround the neck 16 or may surround the handle 12. As another example, the indication element 30 may surround a portion of the handle 12 and/or a portion of the neck 16. As yet another example, the indication element 30 may be disposed on a back-facing surface 12B of the handle 12 and/or the neck 16. As yet another example, the indication element 30 may be disposed on a front-facing surface 12A of the handle 12 and/or the neck 16.

Embodiments are contemplated where the head 14 is replaceable, e.g. removably attached to the neck 16. In such embodiments, after the head 14 has been used for a particular period of time, e.g. three months, the head 14 may be replaced by a another new head. Similarly, embodiments are contemplated where the head 14 and neck 16 are integrally formed, e.g. unitary. In such embodiments, the neck 16 may be removably attached to the handle 12 and can be replaced after a period of time, e.g. three months. Additionally, in such embodiments, the neck 16 may have receiving section which is configured to receive an engagement section 316. As is shown in FIG. 3, the engagement section 316 may comprise detents which act as snap features which preclude or reduce the likelihood that the neck 16 can be removed during normal brushing by a user.

The toothbrush of the present invention may further comprise a power source as discussed previously. The power source may be any suitable element which can provide power to the toothbrush. A suitable example includes batteries. The battery may be sized in order to minimize the amount of real estate required inside the toothbrush. For example, where the electromagnetic source consists of a light emitting element or vibratory motor (used for signaling the user and not vibrating the cleaning elements of the head and/or movement of the head) the power source may be sized relatively small, e.g. smaller than a triple A battery. In such embodiments, the vibratory device may be relatively small. The battery may be rechargeable or may be disposable. Additionally, a plurality of batteries may be utilized. In some embodiments, the power source may include alternating current power as provided by a utility company to a residence. Other suitable power sources are described in U.S. patent application Ser. No. 12/102,881, filed on Apr. 15, 2008, and entitled, "Personal Care Products and Methods".

In some embodiments, the toothbrush of the present invention may be comprised by an oral care system which further comprises an external display which is in signal communication with the toothbrush. In such embodiments, the external display and the toothbrush may communicate with one another via any suitable manner. Some suitable examples of communication between a personal hygiene device, e.g. toothbrush, and an external display are described in U.S. Patent Application Ser. Nos. 61/176,618, entitled, "PERSONAL CARE SYSTEMS, PRODUCTS, AND METHODS", filed on May 8, 2009; 61/180,617, entitled, "PERSONAL CARE SYSTEMS, PRODUCTS, AND METHODS", filed on May 22, 2009; and U.S. Patent Application Publication No. 2008/0109973. In such embodiments, the signal discussed herein may be provided to the user via the external display and/or via the indication element.

Any suitable material may be utilized for the first and second sealing elements. Some examples of suitable material include thermoplastic elastomers, silicone, nitrile butadiene rubber, ethylene propylene diene monomer rubber, or the like. Other suitable examples include thermoplastic elastomers, silicone based materials, NBR (nitrile butadiene rubber), EPDM (ethylene propylene diene monomer), Viton™, etc. Additionally, the sealing elements may be fixed to the handle in any suitable manner, for example, overmolding. In some embodiments, the handle and the sealing elements may overlap to some extent to help reduce the likelihood of contaminants entering between the seam of the sealing elements and the handle. In some embodiments, the material of the sealing elements may also extend along a portion or portions of the handle, to provide a gripping surface, e.g elastomer grip features.

In some embodiments, the sealing elements and/or elastomer grip feature(s) may include visual texture or features which provide a visual signal indicating the flexibility of the toothbrush. For example, as shown in FIG. 12, a toothbrush 1410 may comprise a handle 1412 having a first sealing element 1270 and a second sealing element 1275. The first sealing element 1270 and/or the second sealing element 1275 may comprise rugosities 1480. The rugosities 1480 may provide visual communication to the consumer regarding the flexibility of the toothbrush. As shown, an indication element 1230 may be positioned between the first sealing element 1270 and the second sealing element 1275 which may allow the indication element 1230 to provide a visual signal to the consumer.

As stated previously, the first sealing element and/or second sealing elements as described herein, may be transparent and/or translucent. In such embodiments, the sealing elements may enhance a visual signal be displaying light distributed by the reflective core.

The handle may be any suitable material. Some examples of suitable materials include polypropylene, ABS (acrylonitrile-butadiene-styrene copolymer), ASA (acrylonitrile-styrene-acrylate), copolyester, POM (polyaformaldeyde), combinations thereof, and the like. Additional suitable materials include polypropylene, nylon, high density polyethylene, other moldable stable polymers, the like, and/or combinations thereof. In some embodiments, the handle, the neck, and/or the head, may be formed from a first material and include recesses, channels, grooves, for receiving a second material which is different from the first. For example, the handle may include an elastomeric grip feature or a plurality of elastomeric grip features. The elastomers among the plurality of elastomeric grip features may be similar materials or may be different materials, e.g. color, hardness, combinations thereof or the like.

The elastomeric grip features of the handle may be utilized to overmold, at least in part, a portion of the timer, electromagnetic source, processor, indication element, and/or power source. In such embodiments, these components may be in electrical communication via wiring which can similarly be overmolded. The elastomeric grip features may include portions which are positioned for gripping by the palm of the user and/or portions which are positioned for gripping by the thumb and index finger of the user. These elastomeric grip features may be composed of the same material or may be different, e.g. color, shape, composition, hardness, the like, and/or combinations thereof.

The elastomeric grip features of the handle may be in communication with a channel, groove, and/or recess, in the neck via an external channel, groove, recess and/or via an internal channel, groove, recess. In some embodiments, the elastomeric grip features may be in communication with a channel, groove, and/or recess in the head via an internal channel, groove, and/or recess, and/or an external channel, groove, and/or recess. Alternatively, the grip features of the handle may be discrete elements from the features of the head and/or neck.

In some embodiments, recycled and/or plant derived plastics may be utilized. For example, PET may be utilized in some embodiments. The PET may be bio based. For example, the PET may comprise from about 25 to about 75 weight percent of a terephthalate component and from about 20 to about 50 weight percent of a diol component, wherein at least about one weight percent of at least one of the terephthalate and/or the diol component is derived from at least one bio-based material. Similarly, the terephthalate component may be derived from a bio based material. Some examples of suitable bio based materials include but are not limited to corn, sugarcane, beet, potato, starch, citrus fruit, woody plant, cellulosic lignin, plant oil, natural fiber, oily wood feedstock, and a combination thereof.

Some of the specific components of the PET may be bio based. For example, monoethylene glycol and terephthalic acid may be formed from bio based materials. The formation of bio based PET and its manufacture are described in United States Patent Application Publication Nos. 20090246430A1 and 20100028512A1.

Additionally, as used herein, the term "contact elements" is used to refer to any suitable element which can be inserted into the oral cavity. Some suitable elements include bristle tufts, elastomeric massage elements, elastomeric cleaning elements, massage elements, tongue cleaners, soft tissue cleaners, hard surface cleaners, combinations thereof, and the like. The head may comprise a variety of contact elements. For example, the head may comprise bristles, abrasive elastomeric elements, elastomeric elements in a particular orientation or arrangement, e.g. pivoting fins, prophy cups, or the like. Some suitable examples of elastomeric cleaning elements and/or massaging elements are described in U.S. Patent Application Publication Nos. 2007/0251040; 2004/0154112; 2006/0272112; and in U.S. Pat. Nos. 6,553,604; 6,151,745. The cleaning elements may be tapered, notched, crimped, dimpled, or the like. Some suitable examples of these cleaning elements and/or massaging elements are described in U.S. Pat. Nos. 6,151,745; 6,058,541; 5,268,005; 5,313,909; 4,802,255; 6,018,840; 5,836,769; 5,722,106; 6,475,553; and U.S. Patent Application Publication No. 2006/0080794.

The contact elements may be attached to the head in any suitable manner. Conventional methods include stapling, anchor free tufting, and injection mold tufting. For those contact elements that comprise an elastomer, these elements may be formed integral with one another, e.g. having an integral base portion and extending outward therefrom.

The head may comprise a soft tissue cleanser constructed of any suitable material. Some examples of suitable material include elastomeric materials; polypropylene, polyethylene, etc; the like, and/or combinations thereof. The soft tissue cleanser may comprise any suitable soft tissue cleansing elements. Some examples of such elements as well as configurations of soft tissues cleansers on a toothbrush are described in U.S. Patent Application Nos. 2006/0010628; 2005/0166344; 2005/0210612; 2006/0195995; 2008/0189888; 2006/0052806; 2004/0255416; 2005/0000049; 2005/0038461; 2004/0134007; 2006/0026784; 20070049956; 2008/0244849; 2005/0000043; 2007/140959; and U.S. Pat. Nos. 5,980,542; 6,402,768; and 6,102,923.

For those embodiments which include an elastomeric element on a first side of the head and an elastomeric element on a second side of the head (opposite the first), the elastomeric elements may be integrally formed via channels or gaps which extend through the material of the head. These channels or gaps can allow elastomeric material to flow through the head during an injection molding process such that both the elastomeric elements of the first side and the second side may be formed in one injection molding step.

In such embodiments including a soft tissue cleanser, consumer testing, robot testing, and/or clinical testing may be performed such that an upper threshold of force and a lower threshold of force can be established to provide feedback to the user with regard to the applied force to soft tissue, e.g. tongue. For those embodiments, including a soft tissue cleanser, the toothbrush may comprise an accelerometer or other suitable device for monitoring the orientation of the toothbrush. In combination with the applied force, e.g. brushing force, the processor can determine whether the soft tissue cleanser is being engaged or the cleaning elements are being engaged. The signal or a plurality of signals may be provided to the user as described herein. Providing feedback to the user regarding the applied force to soft tissue can assist the user in preventing damage to the soft tissue, e.g. papillae, while still achieving efficacious cleaning.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A toothbrush in a display package, comprising:
   a handle;
   a head including a plurality of contact elements, the head being attached to a neck, the neck being disposed between the head and the handle and the neck being attached to the handle;
   an indication element disposed between the head and the handle, the indication element being in electrical communication with a power source;
   a switch for connecting the indication element to the power source, the switch having a first position in which the indication element is not energized and a second position for effecting the energizing of the indication element, the switch being placed in the second position when a force is applied to the head; and
   an at least partially translucent package body configured to at least, partially cover the toothbrush, the package body including an open area configured to facilitate application of a force to the head and/or neck through the package body to place the switch in the second position, wherein the package body comprises a first portion and a second portion and the open area allows the second portion to bend with respect to the first portion.

2. The toothbrush in the display package of claim 1, wherein the package body further includes a non-flexible portion disposed proximate the head.

3. The toothbrush in the display package of claim 1, wherein the package body comprises a thermoplastic material.

4. The toothbrush in the display package of claim 1, wherein the package body comprises a rugose area comprising a plurality of ridges which extend generally transversely toward lateral edges of the package body.

5. The toothbrush in the display package of claim 1, wherein a first face comprises a first rugose area having a first plurality of ridges, and a second face comprises a second rugose area having a second plurality of ridges, wherein the first plurality of ridges extend outboard of the toothbrush toward lateral edges of the package body.

6. The toothbrush in the display package of claim 5, wherein at least one of the ridges of the first rugose area comprises a first height of about 2 mm.

7. The toothbrush in the display package of claim 6, wherein at least one of the ridges of the second rugose area comprises a second height which is about equal to the first height.

8. The toothbrush in the display package of claim 5, wherein the first rugose area comprises a first plurality of ridges and the second rugose area comprises a second plurality of ridges, wherein the first plurality of ridges has a greater number of ridges than does the second plurality of ridges.

9. The toothbrush in a display package of claim 1, wherein the package body further comprises an application indicator providing a visual indication to the consumer as to where the package body should be manipulated in order to place the switch in the second position.

\* \* \* \* \*